United States Patent
Kemps

(10) Patent No.: US 12,296,101 B2
(45) Date of Patent: May 13, 2025

(54) ADAPTOR FOR RESPIRATORY ASSISTANCE SYSTEMS

(71) Applicant: Fisher & Paykel Healthcare Limited, Auckland (NZ)

(72) Inventor: David Robert Kemps, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 17/858,842

(22) Filed: Jul. 6, 2022

(65) Prior Publication Data

US 2023/0059409 A1    Feb. 23, 2023

Related U.S. Application Data

(63) Continuation of application No. 15/559,811, filed as application No. PCT/NZ2016/050051 on Mar. 30, 2016, now Pat. No. 11,433,208.

(60) Provisional application No. 62/291,422, filed on Feb. 4, 2016, provisional application No. 62/140,006, filed on Mar. 30, 2015.

(51) Int. Cl.
| | |
|---|---|
| *A61M 16/08* | (2006.01) |
| *A61M 11/00* | (2006.01) |
| *A61M 11/04* | (2006.01) |
| *A61M 15/00* | (2006.01) |
| *A61M 16/06* | (2006.01) |
| *A61M 16/14* | (2006.01) |
| *A61M 16/20* | (2006.01) |

(52) U.S. Cl.
CPC ........ *A61M 16/0816* (2013.01); *A61M 11/04* (2013.01); *A61M 15/009* (2013.01); *A61M 16/0666* (2013.01); *A61M 16/147* (2014.02); *A61M 16/208* (2013.01); *A61M 11/00* (2013.01); *A61M 2240/00* (2013.01)

(58) Field of Classification Search
CPC .......... A61M 16/0816; A61M 16/0666; A61M 16/208; A61M 16/009; A61M 16/201; A61M 16/147
See application file for complete search history.

(56) References Cited

U.S. PATENT DOCUMENTS

| | | | |
|---|---|---|---|
| 4,794,921 A | 1/1989 | Lindkvist | |
| 5,193,532 A | 3/1993 | Moa | |
| 5,501,214 A | 3/1996 | Sabo | |
| 6,014,972 A * | 1/2000 | Sladek | A61M 16/08 128/203.15 |
| 9,084,864 B1 * | 7/2015 | Schroeder | A61M 16/0816 |

(Continued)

FOREIGN PATENT DOCUMENTS

| | | |
|---|---|---|
| EP | 2497515 B1 | 1/2014 |
| WO | WO 2009/117422 A2 | 9/2009 |

(Continued)

*Primary Examiner* — Joseph D. Boecker
*Assistant Examiner* — Thomas W Greig
(74) *Attorney, Agent, or Firm* — Knobbe Martens Olson & Bear LLP

(57) ABSTRACT

An adaptor for a respiratory assistance system delivers aerosols to a patient. The adaptor is lightweight with a small footprint to increase patient comfort. The adaptor has a nozzle and a sealing mechanism to maintain pressure therein regardless of whether the nozzle is inserted into the adaptor. The adaptor is configured to connect to medical tubing and a medicament delivery device.

18 Claims, 24 Drawing Sheets

(56) References Cited

U.S. PATENT DOCUMENTS

| | | | |
|---|---|---|---|
| 9,186,474 B1* | 11/2015 | Rollins, III | A61M 16/0605 |
| 2003/0047185 A1 | 3/2003 | Olsen | |
| 2003/0200970 A1 | 10/2003 | Stenzler et al. | |
| 2006/0120968 A1* | 6/2006 | Niven | A61M 16/14 |
| | | | 128/200.23 |
| 2006/0254579 A1* | 11/2006 | Grychowski | A61M 16/208 |
| | | | 128/203.29 |
| 2007/0119449 A1* | 5/2007 | Boehm | A61M 16/205 |
| | | | 128/95.1 |
| 2008/0264412 A1 | 10/2008 | Meyer | |
| 2008/0283062 A1 | 11/2008 | Esposito | |
| 2010/0071688 A1* | 3/2010 | Dwyer | A61M 16/0816 |
| | | | 128/200.18 |
| 2011/0000487 A1* | 1/2011 | Moa | A61M 16/0666 |
| | | | 128/203.12 |
| 2011/0247616 A1* | 10/2011 | Von Hollen | A61M 15/0026 |
| | | | 128/203.12 |
| 2012/0018525 A1* | 1/2012 | Giroux | B05B 7/2429 |
| | | | 239/1 |
| 2012/0055468 A1* | 3/2012 | Brambilla | A61M 15/009 |
| | | | 128/200.23 |
| 2012/0080033 A1 | 4/2012 | Varga et al. | |
| 2012/0085343 A1* | 4/2012 | Cortez | A61M 16/0816 |
| | | | 128/200.14 |
| 2012/0145149 A1* | 6/2012 | Grychowski | A61M 15/0021 |
| | | | 128/203.15 |
| 2013/0146053 A1* | 6/2013 | Mazela | A61M 16/0858 |
| | | | 137/15.01 |
| 2013/0152925 A1* | 6/2013 | Rahmel | A61M 16/0666 |
| | | | 128/203.12 |
| 2013/0284167 A1* | 10/2013 | Porteous | A61M 16/0057 |
| | | | 128/202.27 |
| 2015/0000652 A1* | 1/2015 | Haveri | A61M 16/0833 |
| | | | 128/202.27 |
| 2015/0224278 A1 | 8/2015 | Addington | |
| 2018/0043126 A1 | 2/2018 | Kemps | |

FOREIGN PATENT DOCUMENTS

| | | |
|---|---|---|
| WO | WO 2014/144054 A1 | 9/2014 |
| WO | WO 2014/193847 A1 | 12/2014 |
| WO | WO 2016/159784 | 10/2016 |

* cited by examiner

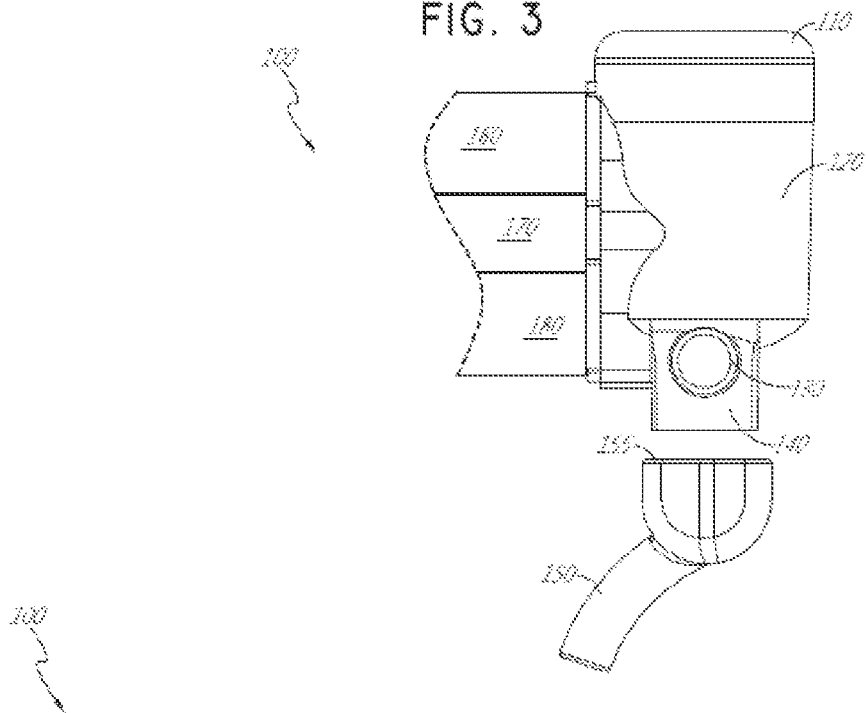
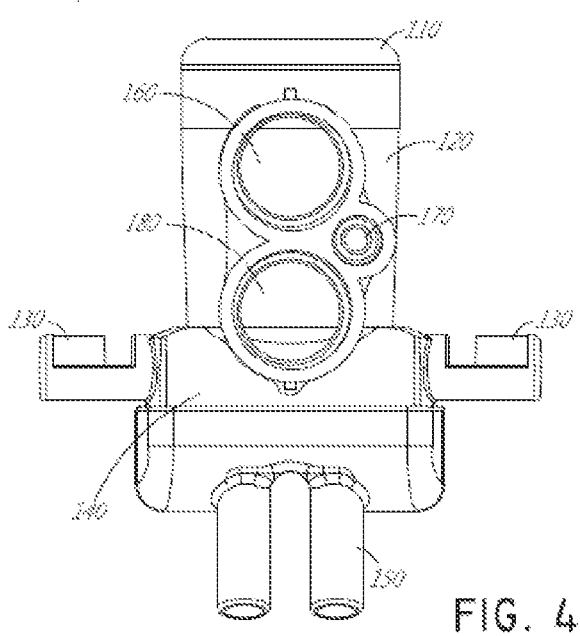

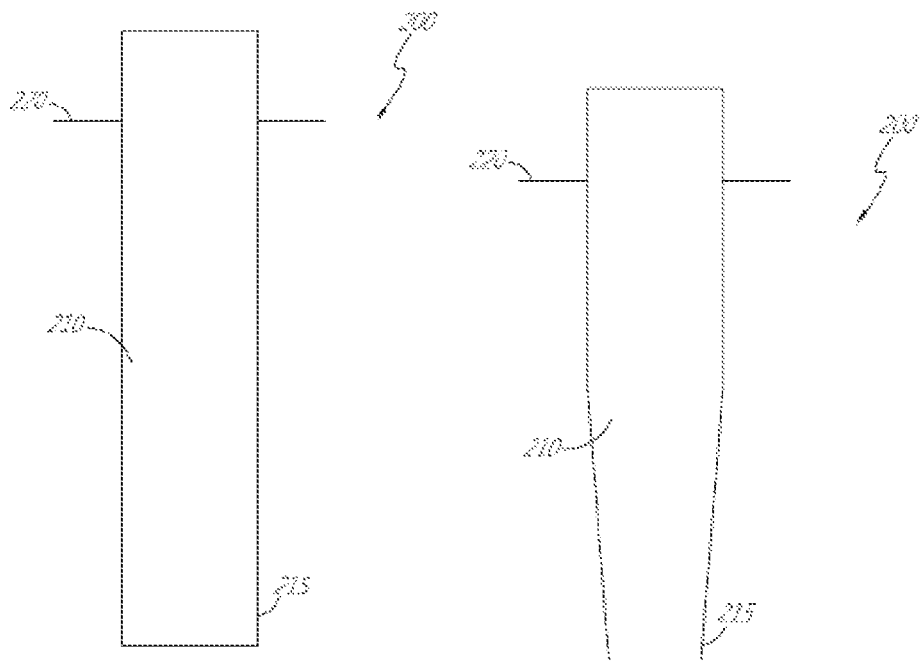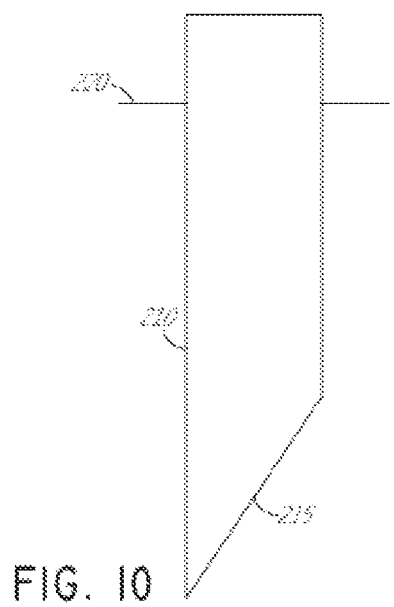

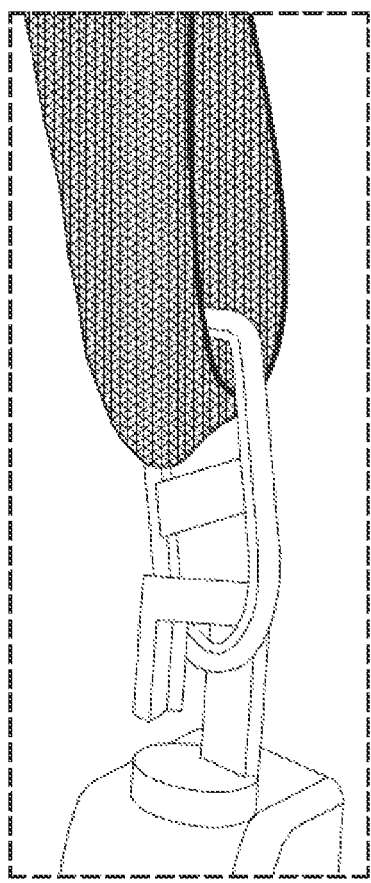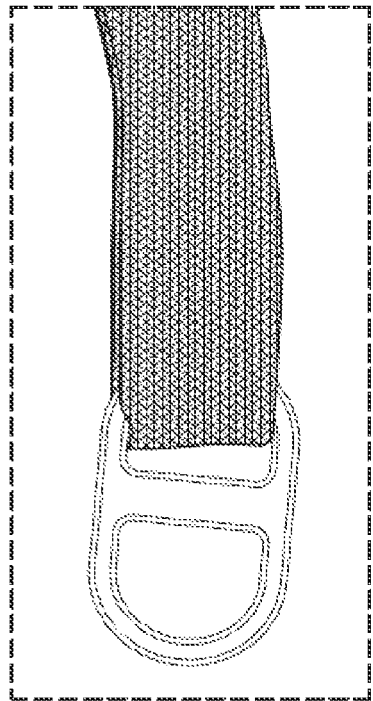

ADAPTOR FOR RESPIRATORY ASSISTANCE SYSTEMS

INCORPORATION BY REFERENCE TO ANY PRIORITY APPLICATIONS

This application is continuation of U.S. application Ser. No. 15/559,811, filed Sep. 19, 2017 and issued as U.S. Pat. No. 11,433,208 on Sep. 6, 2022, which is a U.S. national stage application of International Application No. PCT/NZ2016/050051, filed Mar. 30, 2016, which claims the priority benefit of and incorporates by reference in the entirety U.S. Provisional Application No. 62/140,006, filed Mar. 30, 2015 and U.S. Provisional Application No. 62/291,422, filed Feb. 4, 2016.

FIELD OF THE DISCLOSURE

The present disclosure generally relates to respiratory assistance systems configured to deliver medical gases to a patient. More particularly, the present disclosure relates to an adaptor configured to couple with a respiratory assistance system to deliver medical gases and aerosolised substances to an infant.

BACKGROUND

Gases delivery adaptors are configured to couple between a medical apparatus and a patient interface to aid with the delivery of gases or aerosolised substances.

Respiratory systems may deliver conditioned gases to a patient. Gases are heated and humidified prior to delivery to mimic the transformation of gases that occurs as they travel from the nose to the lungs in a healthy individual. This improves airway defence and gases exchange in the lungs when compared with the delivery of cold, dry gases to a patient. Medicament delivery devices, for example, nebulisers, capillary aerosol generators or metered dose inhalers (MDIs) couple with respiratory systems to deliver medicaments, such as aerosols, dry powders or aerosolised surfactant to a patient during respiratory treatment. Adaptors are used to couple medicament delivery devices with respiratory systems.

Bubble Continuous Positive Airway Pressure (CPAP) is a therapy that can provide respiratory support to infants. This includes maintaining the functional residual capacity of the lungs, which can help to prevent the airways from closing and maintains the energy reserves of infants without requiring invasive ventilation. Gases delivered to patients via a bubble CPAP system may be heated and humidified, which minimises airway drying and inflammation, while improving secretion clearance and ventilation. As a result, use of a conditioned bubble CPAP system may reduce the time an infant is hospitalised. Bubble CPAP therapy can be delivered using a patient interface, such as a mask, or nasal prongs. Aerosols can be administered to a patient through the patient interface.

SUMMARY

A medical gases delivery adaptor is disclosed herein in various embodiments. The adaptor includes a housing with an inlet port and an outlet port that couples with medical tubing. A patient interface couples with the housing to deliver gases to a patient. The housing can be sealed, for example, with a valve. The housing can be configured to receive a nozzle through the valve. The nozzle may fluidly couple with a medicament delivery device, and can be configured to deliver aerosolised gases, medicament or surfactant to the patient. The nozzle can be removable.

For purposes of summarising the present disclosure, certain aspects, advantages and novel features of the disclosed apparatus and systems have been described herein. It is to be understood that not necessarily all such advantages may be achieved in accordance with any particular embodiment of the disclosure. Thus, the disclosed apparatus and systems may be embodied or carried out in a manner that achieves or optimises one advantage or group of advantages as taught herein without necessarily achieving other advantages as may be taught or suggested herein.

According to at least one aspect of the present disclosure, a respiratory system component can include one, some, or all of the following features, as well as other features described herein. The respiratory system component includes a housing, an inlet port, and an outlet port. The housing includes a first end and a second end. The housing defines a passageway between the first end and the second end. The inlet port is coupled with the housing. The inlet port is configured to couple with a first conduit. The outlet port is coupled with the housing. The outlet port is configured to couple with a second conduit. The first end of the housing is sealed by a valve. The second end of the housing is configured to couple with a patient interface.

The housing can include at least one clip configured to facilitate attachment of a headgear to the respiratory system component. The respiratory system component can include a coupling surface in fluid communication with the second end of the housing. The coupling surface can be configured to receive the patient interface by a friction fit. The patient interface can include nasal prongs or a nasal mask. The valve can include a duckbill valve. The valve can be configured to receive a nozzle. The nozzle can be configured to fluidly connect the passageway of the housing with a medicament delivery device.

According to at least one aspect of the present disclosure, a respiratory system component can include one, some, or all of the following features, as well as other features described herein. The respiratory system component includes an inspiratory tube, an expiratory tube, a patient interface, an adaptor, a removable nozzle, and a valve. The patient interface is configured for delivery of respiratory gases and aerosolised substances to a patient. The adaptor joins the inspiratory tube, the expiratory tube, and the patient interface.

The removable nozzle may be configured to be in fluid connection with a delivery device that provides an aerosolised substance. The delivery device may be a nebuliser.

The valve may be self-sealing. The valve may be a duckbill valve or a slit valve. The removable nozzle may be removably insertable into the adaptor through the valve.

The adaptor may be configured to have a small volume to reduce dead space. A volume of dead space in the adaptor may be less than a tidal volume of a patient.

The patient interface may include nasal prongs. The nasal prongs may be removably attachable to the adaptor. The nasal prongs may be permanently attached to or integrated with the adaptor.

The removable nozzle may be packaged with the adaptor. The removable nozzle may be packaged with the delivery device. The nozzle may be cylindrical. The nozzle may be configured to improve the efficiency of gases flow around the nozzle. The nozzle may be fluidly connected with the patient interface such that deposition within the adaptor of an aerosolised substance delivered through the nozzle is reduced.

A distance between the nozzle and the patient interface may be less than about 10 mm. A distance between the nozzle and the patient interface may be less than about 5 mm. A distance between the nozzle and the patient interface may be less than about 3 mm.

The nozzle may have a circular cross-section and may be configured to reduce deposition of an aerosolised substance.

The nozzle may be configured to be connected to the delivery device through a tube. The tube may be short to reduce deposition of an aerosolised substance within the tube. The length of the tube may be configured to reduce the total mass on a patient's face and/or chest. The tube may be configured to allow the delivery device to be removable from the nozzle.

According to at least one aspect of the present disclosure, a respiratory system component can include one, some, or all of the following features, as well as other features described herein. The respiratory system component includes a housing, an inlet port, and an outlet port. The housing includes a first end and a second end and defines a passageway between the first end and the second end. The inlet port is attached to the housing. The inlet port is configured to couple with a first conduit. The outlet port is attached to the housing. The outlet port is configured to couple with a second conduit. The first end is sealed by a valve. The second end is configured to couple with a patient interface.

The housing may include at least one clip configured to facilitate attachment of a headgear to the respiratory system component. The respiratory system component may include a coupling surface in fluid communication with the second end of the housing. The coupling surface may be configured to receive the patient interface by a friction fit. The patient interface may be nasal prongs or a nasal mask. The valve may be a duckbill valve. The valve may be configured to receive a nozzle. The nozzle may be configured to fluidly connect the passageway of the housing with a medicament delivery device.

According to at least one aspect of the present disclosure, an adaptor for a respiratory system that aids in providing respiratory medicament to a patient can include one, some, or all of the following features, as well as other features described herein. The adaptor includes a housing, an inlet port, a pressure port, and an outlet port. The housing includes a sealing portion and a coupling surface. The inlet port includes a first end attached to the housing and a second end configured to couple to an inspiratory tube. The pressure port includes a first end attached to the housing and a second end configured to couple with a pressure line. The outlet port includes a first end attached to the housing and a second end configured to couple with an expiratory tube.

The adaptor may include a plurality of clips that protrude from first and second sides of the coupling surface. The clips may include any of C-shaped protrusions, L-shaped protrusions, clipping mechanisms, adhesives, or hook and loop mechanisms. The plurality of clips may be positioned on a slidable and/or rotatable bar or cord.

The sealing portion may include a valve configured to seal the housing. The valve may be configured to provide access into the housing while maintaining a sealed system. The valve may be a duckbill valve or a slit valve.

The adaptor may be configured to receive a nozzle that can be removably inserted into the adaptor through the sealing portion. Alternatively, the adaptor may be permanently integrated with a nozzle.

The coupling surface may be configured to be removably coupled with a patient interface. Alternatively, the coupling surface may be configured to be permanently coupled with a patient interface.

According to at least one aspect of the present disclosure, a respiratory system can include one, some, or all of the following features, as well as other features described herein. The respiratory system includes an adaptor, a patient interface, and a nozzle. The adaptor includes a sealing portion, a coupling surface, an inlet port, a pressure port, and an outlet port. The patient interface is coupled to the coupling surface. The nozzle includes a ledge. The nozzle is configured to be inserted into the sealing portion of the adaptor such that the ledge rests on the sealing portion of the adaptor.

The respiratory system may include a medicament delivery device. The medicament delivery device may be configured to couple to the nozzle. The medicament delivery device may be coupled to the nozzle via a tube. The medicament delivery device may be coupled to the nozzle through a coupling mechanism. The medicament delivery device may be at least one of a nebulizer, a capillary aerosol generator, and a metered dose inhaler.

The patient interface may be coupled with the coupling surface via a friction fit. The patient interface may include a hollow complementary region that is configured to receive the coupling surface. The coupling surface may be configured to receive the hollow complementary region of the patient interface. A partial barrier may exist between the adaptor and the first end of the coupling surface. The patient interface may be permanently coupled with the adaptor using at least one of adhesives, snap-fit mechanisms, and welding techniques. Alternatively, the patient interface may be removably coupled with the adaptor using at least one of adhesives and mechanical mechanisms. The coupling surface may have a rectangular cross-section.

The patient interface may be at least one of a respiratory interface, a diffuser, a trocar, or a catheter. The respiratory interface may be at least one of nasal prongs, a nasal mask, an oral mask, a combined nasal and oral mask, a tracheal mask, or a nasal pillow.

The respiratory system may include an intermediate tube system configured to couple with the adaptor. The intermediate tube system may include an intermediate inspiratory tube configured to couple with the inlet port. The intermediate tube system may include an intermediate expiratory tube configured to couple with the outlet port.

The nozzle may be permanently integrated with the adaptor. The nozzle may be sealed with a cap coupled to the adaptor using a tether or a chain. The respiratory system may include a connector attached to the nozzle. The connector may be configured to couple a tube to the nozzle.

The connector may include an angled connection configured to couple the tube to the nozzle. The connection angle may be about 90 degrees. The connection angle may be between about 90 degrees and about 180 degrees.

The sealing portion may include a valve configured such that the adaptor remains sealed around the nozzle. The valve may reseal itself upon removal of the nozzle.

According to at least one aspect of the present disclosure, a nozzle for an adaptor of a respiratory system can include one, some, or all of the following features, as well as other features described herein. The nozzle includes a body and a ledge. The body includes a first end and a second end, the first end configured to couple with a medicament delivery device. The ledge is configured to rest on a sealing portion of the adaptor.

The first end may be configured to couple with a medicament delivery device. The medicament delivery device may be at least one of a nebulizer, a capillary aerosol generator, and a metered dose inhaler. The first end may be configured to couple with a tube. The second end may form an angled cut-off.

The body of the nozzle may include a smooth inner surface. The body may be tapered. The diameter of the second end may be less than the diameter of the first end. The diameter of the first end may be between about 3 mm and about 10 mm, and the diameter of the second end is between about 1 mm and about 5 mm. The nozzle may be cylindrical. The inner diameter of the body may be between about 1 mm and about 20 mm.

According to at least one aspect of the present disclosure, a respiratory system component can include one, some, or all of the following features, as well as other features described herein. The respiratory system component includes an inspiratory tube, an expiratory tube, an interface configured for drug delivery, an adaptor located between the inspiratory tube and the expiratory tube, and a nozzle. The nozzle is configured to extend from an opening in the adaptor.

The inspiratory tube and the expiratory tube may be parallel. The nozzle may be oriented perpendicular to the inspiratory tube and the expiratory tube. Gas flow through the nozzle and gas flow through the inspiratory tube within the adaptor may be in the same direction. The adaptor may be asymmetrical.

The nozzle may protrude from the surface of the adaptor. The drug delivery may be via a nebuliser. The adaptor may be configured to have a smaller volume to reduce dead space. A volume of dead space in the adaptor may be less than a tidal volume of a patient.

The interface may include nasal prongs. The nasal prongs may be attachable to the adaptor. Alternatively, the nasal prongs may be integrated with the adaptor.

The nozzle may be cylindrical. The nozzle may be configured to maximize the efficiency of gases flow around the nozzle. The nozzle may be fluidly connected with the interface such that drug deposition within the adaptor is reduced. The nozzle may have a circular cross-section. The nozzle may be configured to reduce drug deposition.

The nozzle may be connected to the drug delivery device through a tube. The length of the tube may be optimised to reduce drug deposition. The length of the tube may be configured to minimize the total mass on a patient's face and/or chest. The tube may be configured to allow the drug delivery device to be removable from the adaptor.

BRIEF DESCRIPTION OF THE DRAWINGS

These and other features, aspects and advantages of the present disclosure will be described with reference to the following drawings, which are illustrative but should not be limiting of the present disclosure.

FIG. 3 illustrates an exploded side view of the adaptor of FIG. 2.

FIG. 4 illustrates a front view of the adaptor of FIG. 2.

FIGS. 8-10 illustrate different embodiments of removable nozzles.

FIGS. 17A-17B illustrates an embodiment of a removable attachment for an interface stabilising mechanism.

DETAILED DESCRIPTION

Figure 1:
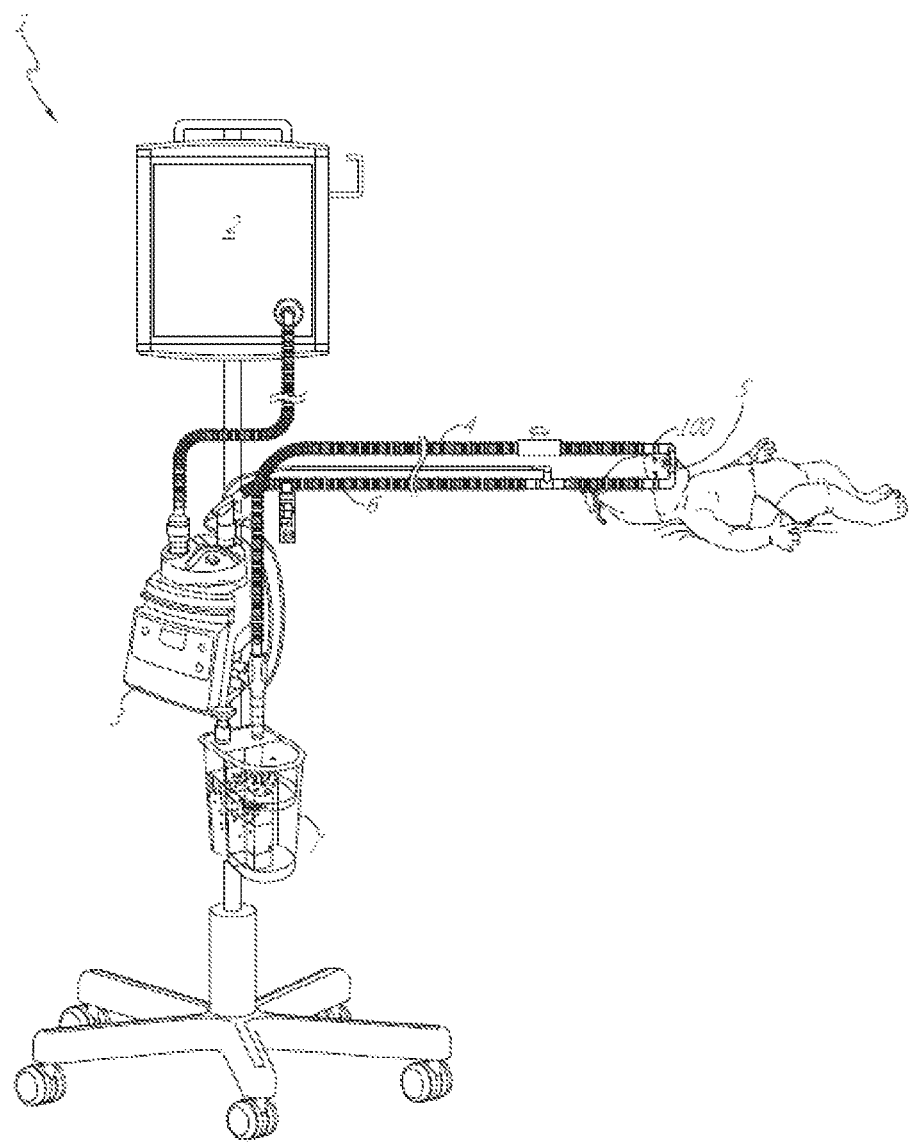
FIG. 1 illustrates an example respiratory system.
Figure 2:
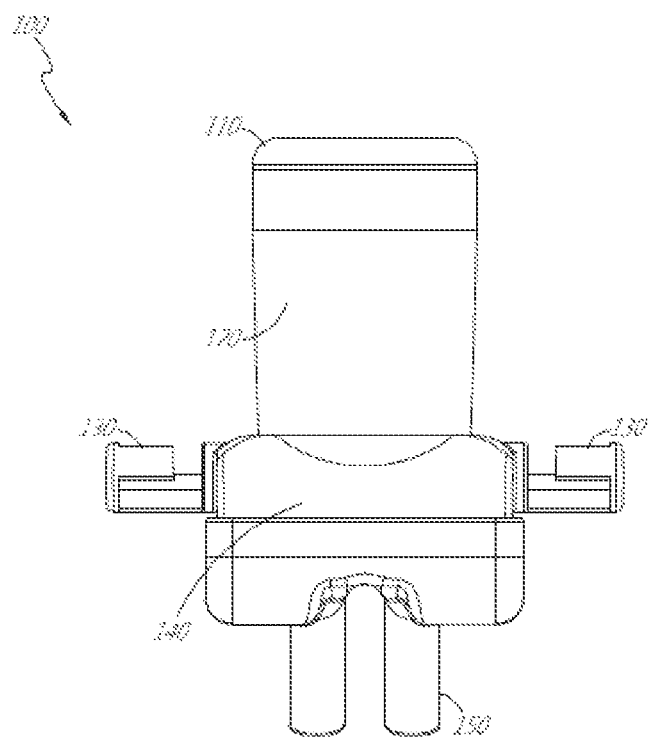
FIG. 2 illustrates a rear view of an adaptor for a respiratory system according to an embodiment of the disclosure.

FIG. 1 illustrates an example of a respiratory assistance system 1 configured to provide respiratory gases to a patient. In the illustrated embodiment, the patient is an infant, however the patient could also be an adult or a child. The respiratory assistance system 1 can include a gases source 2 that supplies gases to a humidification apparatus 3. The humidification apparatus 3 can condition the gases before passing them via an inspiratory tube 6 to a patient by a patient interface 5. In some examples, the patient interface 5 can be nasal prongs or a nasal mask. In some embodiments, the patient interface 5 may be configured to be sealingly positioned on the face of the patient. Upon exhalation of the patient, the gases are passed through an expiratory tube 4 to a pressure regulating device 7. In some embodiments, the pressure regulating device 7 is a ventilator or bubbler. The patient interface 5 couples to the inspiratory tube 6 and to the expiratory tube 4 using an adaptor 100. Alternative respiratory assistance systems can include a single tube, for example inspiratory tube 6, which can allow exhalation to occur through the patient interface 5 and/or the adaptor 100. Thus, the adaptor 100 can couple the patient interface 5 to the single tube system.

Prior art adaptors configured to deliver aerosols to a patient are bulky and heavy in use and may cause discomfort to the patient. As a result, such adaptors are often only temporarily coupled to the patient during aerosol treatment. This results in high user effort to install and then to remove these adaptors, which can impact the treatment delivered to the patient. Other prior art adaptors provide poor sealing mechanisms between the adaptor and the coupling region of a medicament delivery device, which causes significant pressure losses in the system.

FIGS. 2-6 illustrate an example embodiment of an adaptor 100 that addresses many of the disadvantages of prior art adaptors. The adaptor 100 can include features that allow it to remain in place throughout the use of the medical system. Thus, the adaptor 100 may not require removal following aerosol treatment of the patient. For example, the adaptor 100 can form an integral part of the patient interface 5. This can include, for example, a continuous positive airway pressure (CPAP) interface and/or may include features that enable delivery of medicament via the integrated adaptor 100.

Prior art systems require a user to remove the patient interface temporarily to replace it with a medicament delivery interface, following which the patient interface is restored to the patient. This configuration may cause patient discomfort and may reduce the efficacy of the treatment. As a result, a patient may be more likely to undergo invasive procedures, due to disturbances during treatment.

In some examples, the adaptor 100 is integrated with the patient interface 5. Integration of the adaptor 100 and the patient interface 5 can reduce the number of steps a user is expected to perform to install and remove the adaptor 100, improving the usability of the system. Use of the adaptor 100 throughout the treatment duration can reduce the likelihood of complications during treatment, and reduces the number of disturbances during treatment.

The adaptor 100 can include a sealing portion 110, a housing 120, one or more clips 130, and a coupling surface 140. In some examples, a patient interface 150 can be coupled to the adaptor 100 at the coupling surface 140. In some embodiments, the adaptor 100 can include an inlet port 160, a pressure port 170, and an outlet port 180. A first end of the inlet port 160 and a first end of the outlet port 180 can be connected to the housing 120 of the adaptor 100. A second end of the inlet port 160 can be configured to couple with an inspiratory tube and a second end of the outlet port 180 can be configured to couple with an expiratory tube. A first end of the pressure port 170 can connect to the housing 120 of the adaptor 100 and a second end of the pressure port 170 can be configured to couple with a pressure line (not shown). In some examples, the inlet port 160 can be positioned such that it is proximal to the sealing portion 110. In some embodiments, the outlet port 180 can be positioned such that it is proximal to the coupling surface 140. In some embodiments, the inlet port 160 and the outlet port 180 have swapped positions relative to each other, such that the outlet port 180 can be positioned proximal to the sealing portion 110 and the inlet port 160 can be positioned proximal to the coupling surface 140.

The housing 120 can include a substantially hollow cylindrical body. The shape of the housing 120 can be optimised to reduce resistance to flow within the housing 120. In some embodiments, the shape of the housing 120 can minimise volume within the housing 120. This can reduce dead space, and thus the build-up of carbon dioxide within the housing 120. The housing 120 can be compact which can reduce the weight and bulk of the housing 120 and improve patient comfort. A first end of the housing 120 can include a sealing portion 110. A second end of the housing 120 can be connected with the coupling surface 140. In some examples, the housing 120 can be configured to both receive gases via an inspiratory tube and aid the exit of gases via an expiratory tube. In some embodiments, the housing 120 can have different shapes, for example, rectangular, square, hexaganol, or semi-circular.

As will be discussed in more detail below, in some examples, the nozzle 200 can be cylindrical and/or frustoconical. The housing 120 of the adaptor 100 can be configured to be complementary to the nozzle 200. This complementary configuration can help to minimize resistance to flow for a given diameter of the housing 120, as the housing 120 can extend evenly around the nozzle 200. In some examples, this can maximize the available surface area about the nozzle 200 that the gases can flow. A cylindrical and/or frustoconical shape can also reduce the bulk of the adaptor 100 as a result of the size of the housing 120 relative to the face of the patient. In some embodiments, this is because the cylindrical/frustoconical shape maximizes the size about the nozzle as the cylindrical/frustoconical shape allows all points to extend evenly about the nozzle. By contrast, a square shape would increase the bulk of the adaptor 100 that covers the patient's face (e.g. an infant) as a minimum distance between some of the square edges could cause the corners of the square adaptor 100 to have an increased distance, and therefore create a greater bulk within the adaptor 100.

The coupling surface 140 can be configured to form a surface to which the patient interface 150 couples. In some embodiments, the coupling between the patient interface 150 and the coupling surface 140 can be a friction fit. As shown in FIG. 3, the patient interface 150 can include a substantially hollow complementary region 155 that is configured to receive the coupling surface 140. In some embodiments, the coupling surface 140 can be configured to receive the complementary region 155 of the patient interface 150. In some embodiments, the patient interface 150 can be permanently coupled with the adaptor 100. This can provide a fully integrated adaptor, which may improve the usability of the adaptor 100.

In some examples, the patient interface 150 can include nasal prongs as illustrated in FIGS. 3-4 and 6-7. In some embodiments, the patient interface 150 can include respiratory interfaces such as, but not limited to, a nasal mask, oral mask, combined nasal and oral mask, tracheal mask, or nasal pillows. In some embodiments, the adaptor 100 can be adapted for use in a surgical application. The patient interface 150 can include a diffuser, trocar, or catheter.

As illustrated, the coupling surface 140 can be rectangular in cross-section. In some embodiments, the coupling surface 140 can include a first end that is fluidly connected with the housing 120. In some embodiments, the coupling surface 140 can include a second end that is configured to couple with the patient interface 150. The second end of the coupling surface 140 can allow fluid communication between the housing 120 and the patient interface 150. In some embodiments, a partial barrier can exist between the housing 120 and the first end of the coupling surface 140. An orifice can thus maintain fluid communication between the housing 120 and the patient interface 150. The orifice can direct the flow of gases toward the patient interface 150. In some examples, the orifice can control the pressure of the gases flow as it enters the patient interface 150.

In some embodiments, the patient interface 150 can be configured to removably couple with the coupling surface 140. In some examples, the patient interface 150 can be coupled with the coupling surface 140 using adhesives or mechanical mechanisms such as snap-fit mechanisms. In some embodiments, the patient interface 150 can be permanently attached to the coupling surface 140 using adhesives, snap-fit mechanisms, or welding techniques.

The sealing portion 110 can form a plug, membrane, or closure at the first end of the housing 120. As illustrated, in some embodiments the sealing portion 110 can include a valve 190 to seal the housing 120. The valve 190 can provide access into the housing 120 while maintaining a sealed system. In some embodiments, an instrument, nozzle, or medical tube, can be inserted or removed from the housing 120 through the valve 190 without a significant change in the pressure within the housing 120. Upon removal of the instrument, nozzle, or medical tube, the valve 190 is configured to reseal the first end of the housing 120. In some embodiments, the valve 190 can be, for example, a duckbill valve, a slit valve, or any other type of valve that seals the system but can allow the nozzle to be inserted into the housing 120. In some examples, the duckbill valve can be circular. A duckbill valve can allow the nozzle 200 to be inserted into the housing 120 independent of orientation. This can help to increase the case of assembly.

In some embodiments, the sealing portion 110 can include a cap. The cap can be tethered to the adaptor 100. The tether can prevent misplacement of the cap. The cap can also provide an intuitive and simple way for a user to seal the housing 120 while allowing access for an instrument, nozzle or medical tube.

The clips 130 can protrude from first and second sides of the coupling surface 140. In some embodiments, as illustrated in FIG. 4, the first and second sides of the coupling surface 140 can be substantially perpendicular to the first and second ends of the coupling surface 140. The clips 130 can be configured to removably attach to an interface stabilising mechanism, such as headgear or a hat or bonnet.

In some examples, the clips 130 can engage a removable attachment that is attached to an interface stabilising mechanism, such as headgear or a hat or bonnet. In some examples, the removable attachment is a loop. In some embodiments, the removable attachment is a clipping mechanism. An example of the removable attachment is illustrated in FIGS. 17A and 17B. As illustrated in FIG. 17A, the clip 130 can hook onto a loop of the removable attachment. The removable attachment can be looped onto a length of fabric that is attached to a portion of the interface stabilising mechanism. FIG. 7B illustrates the removable attachment of the interface stabilising mechanism.

Figure 5:
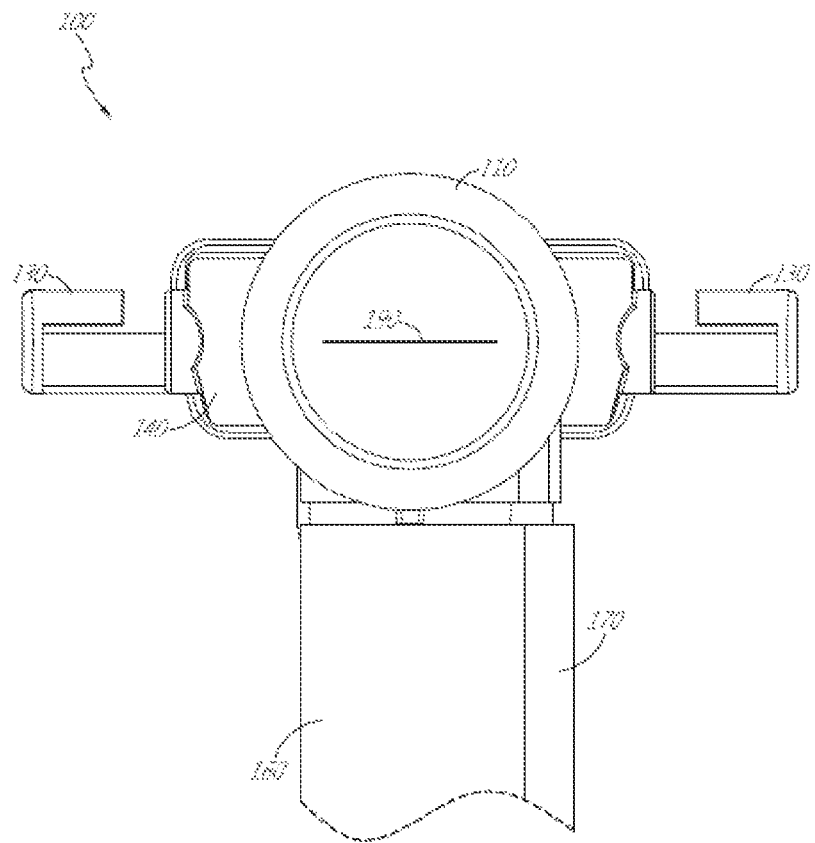
FIG. 5 illustrates a top view of the adaptor of FIG. 2.

In some embodiments, as illustrated in FIG. 5, the clips 130 can include C-shaped protrusions. In some embodiments, the clips 130 can include L-shaped protrusions, clipping mechanisms, adhesives, or hook and loop mechanisms. The clips 130 can be configured to attach to the interface stabilising mechanism in a simple yet effective mechanism. This can enable the patient interface 150 to be positioned correctly and stably on the patient.

In some embodiments, the clips 130 can be configured to permanently attach to an interface stabilising mechanism.

In some embodiments, the clips 130 can be positioned on first and second sides of the housing 120. For example, the clips 130 can be positioned at or near the second side of the housing 120.

In some embodiments, the clips 130 can be configured to be mobile clips. For example, the clip 130 can be positioned on a slidable and/or rotatable bar or cord. In this way, the position of the clips 130 can be rotated or altered to simplify the attachment of the patient stabilising mechanism to the adaptor 100.

Figure 6:
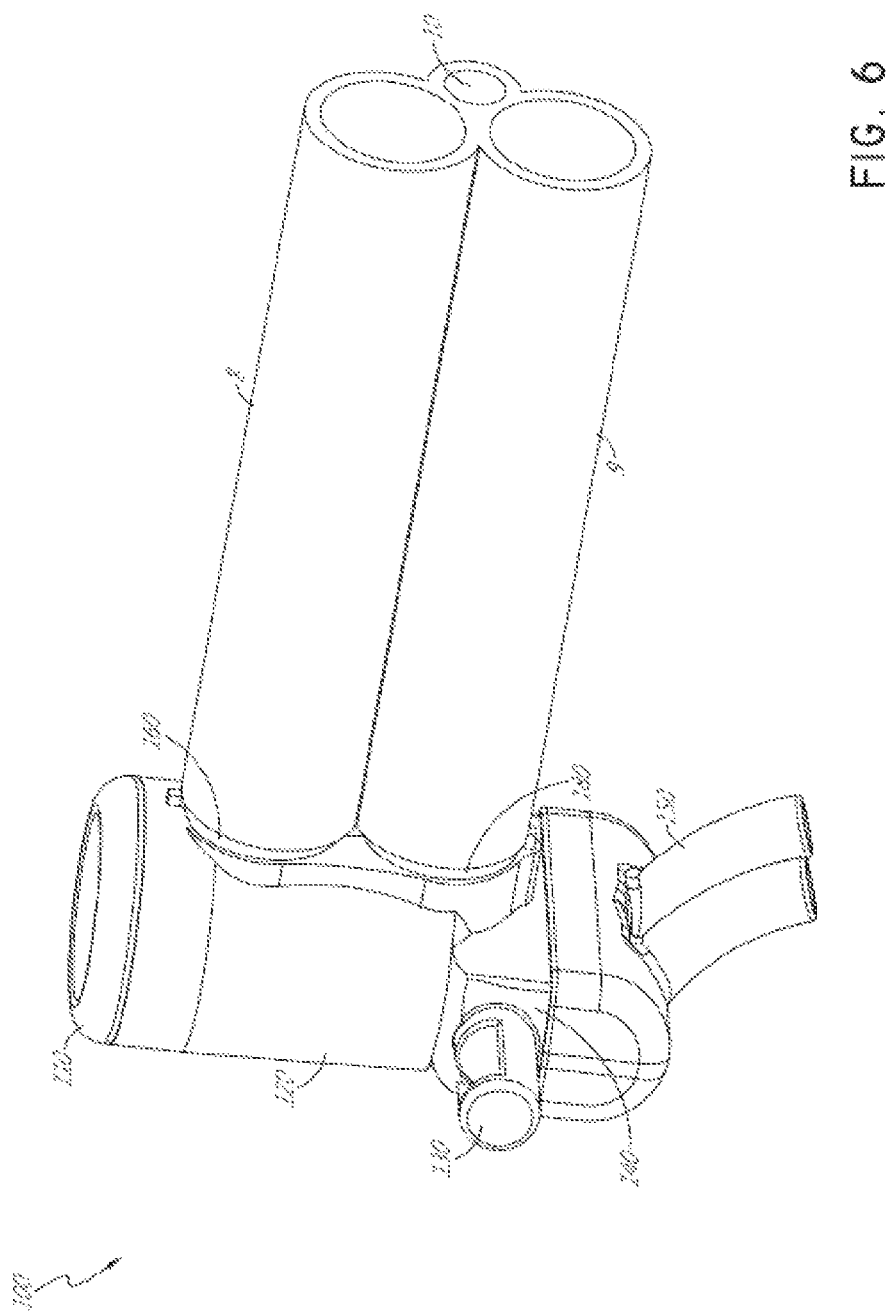
FIG. 6 illustrates the adaptor of FIG. 2 coupled with an intermediate tube system.

FIG. 6 illustrates an embodiment wherein the adaptor 100 is configured to couple with an intermediate tube system that includes an intermediate inspiratory tube 8, an intermediate expiratory tube 9, and an intermediate pressure line 10. In some examples, the intermediate inspiratory tube 8 can be configured to couple with the inlet port 160, and the intermediate expiratory tube 9 can be configured to couple with the outlet port 180. In some examples, the intermediate tube system can be configured to extend above the head of the patient and couple with the inspiratory tube 6 and the expiratory tube 4 distal to, or at an end away from, the patient. The intermediate tube system can be more rigid than a conventional tube set such that it is able to hold its shape without contacting the patient. The intermediate tube system can help to reduce the weight perceived by the patient by spreading out or increasing the distribution of forces from the interface and tubing, reducing patient discomfort.

In some examples, the adaptor 100 can include a single, integrated component that is able to couple with respiratory tubes and also with the patient interface 150. In some embodiments, the adaptor 100 can have an optimised construction that allows it to maintain a small footprint which can increase patient comfort. In some examples, the small footprint of the adaptor 100 can allow the adaptor 100 to provide aerosolized therapy while still retaining the size and weight of a normal CPAP interface. This interface can allow the adaptor 100 to have similar usability as other CPAP interfaces.

Figure 13:
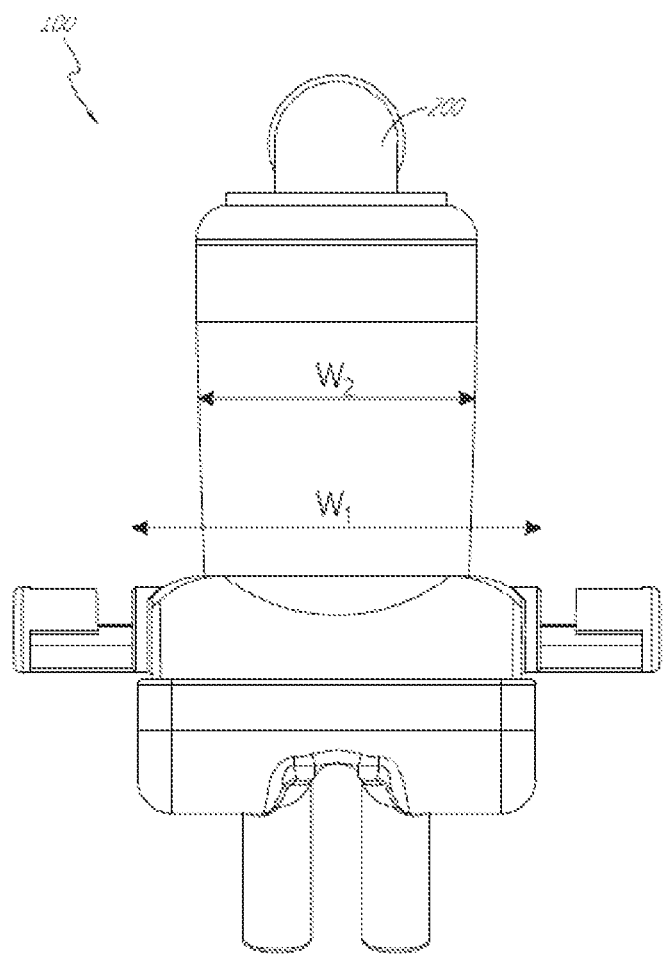
FIG. 13 illustrates a rear view of the adaptor of FIG. 11.
Figure 14:
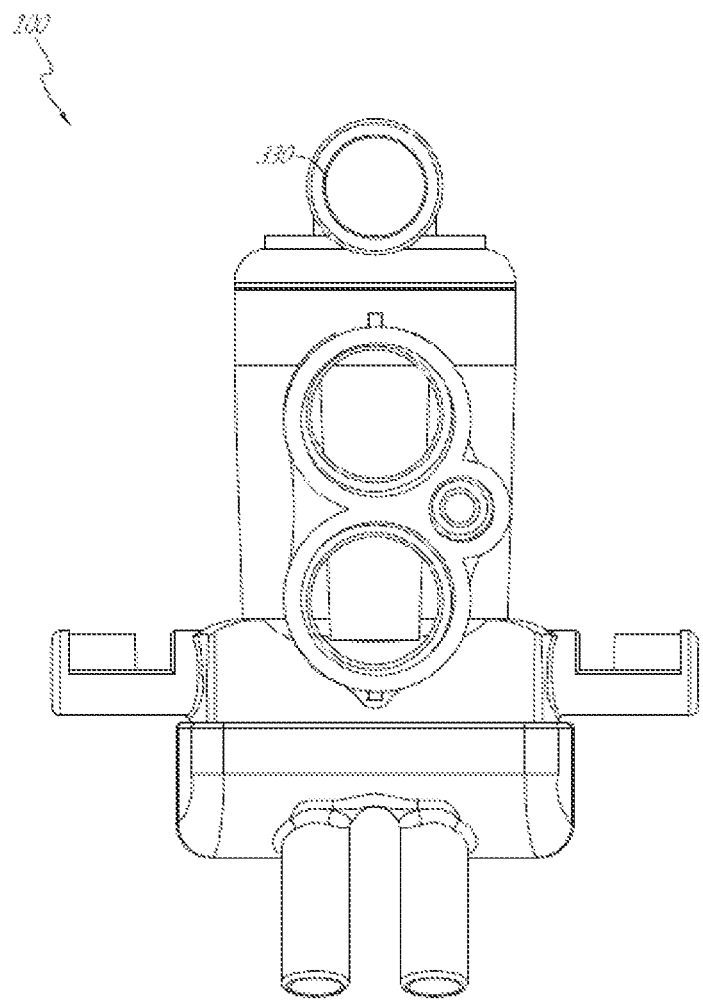
FIG. 14 illustrates a front view of the adaptor of FIG. 11.
Figure 15:
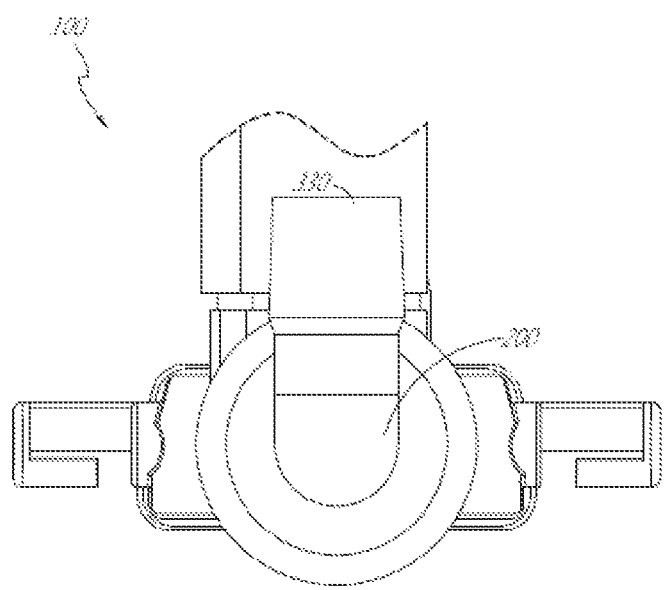
FIG. 15 illustrates a top view of the adaptor of FIG. 11.

In some examples, the adaptor 100 is configured such that it is not bulky or heavy for the patient, and thus may be perceived to be less obstructive. To increase patient comfort, the size of the adaptor 100 can be reduced to limit the amount the adaptor 100 covers/blocks the patient's face from view. As illustrated in FIG. 13, in some examples the width $W_2$ can be the same width or smaller than $W_1$. In some examples, the width $W_1$ can measure approximately 20 mm. The small size of the adaptor 100 can be achieved using a number of different configurations. For example, the adaptor 100 can have an integrated design wherein the nozzle 200 is configured to enter into the housing 120 of the adaptor 100. In other examples, the inlet port 160 and outlet port 180 of the adaptor 100 can come off the side of the housing 120 without adding much bulk. As will be discussed in more detail below, the location of the inlet and outlet ports 160, 180 can also allow easy fitting with tubing.

In other examples, patient comfort can be increased by reducing the weight of the adaptor 100. For example, the adaptor 100 and interface 150 can be configured such that it does not weigh more than any baby for which the device could be configured for use (e.g. preterm baby). In some examples, the weight of the adaptor 100 and interface 150 can weigh approximately 100-500 grams. In other examples, the adaptor 100 and interface 150 can weigh less than 100 grams or more than 500 grams. In other examples, the adaptor 100 and interface 150 can weigh between 15-30 grams. In other examples, the adaptor 100 and interface 150 can weigh 15 grams, 16 grams, 17 grams, 18 grams, 19 grams, 20 grams, 21 grams, 22 grams, 23 grams, 24 grams, 25 grams, 26 grams, 27 grams, 28 grams, 29 grams, or 30 grams.

FIGS. 7-10 illustrate a nozzle 200 that can be configured to be removably inserted into the adaptor 100. In some embodiments, the nozzle 200 can be configured to insert into the housing 120 via the sealing portion 110 of the adaptor 100. For example, the nozzle 200 can be configured to insert through the valve 190. The valve 190 can be configured to receive the nozzle 200 such that the adaptor 100 remains sealed around the nozzle 200. In some examples, the valve 190 reseals itself upon removal of the nozzle 200 such that no or a minimal pressure loss occurs within the system.

Figure 7:
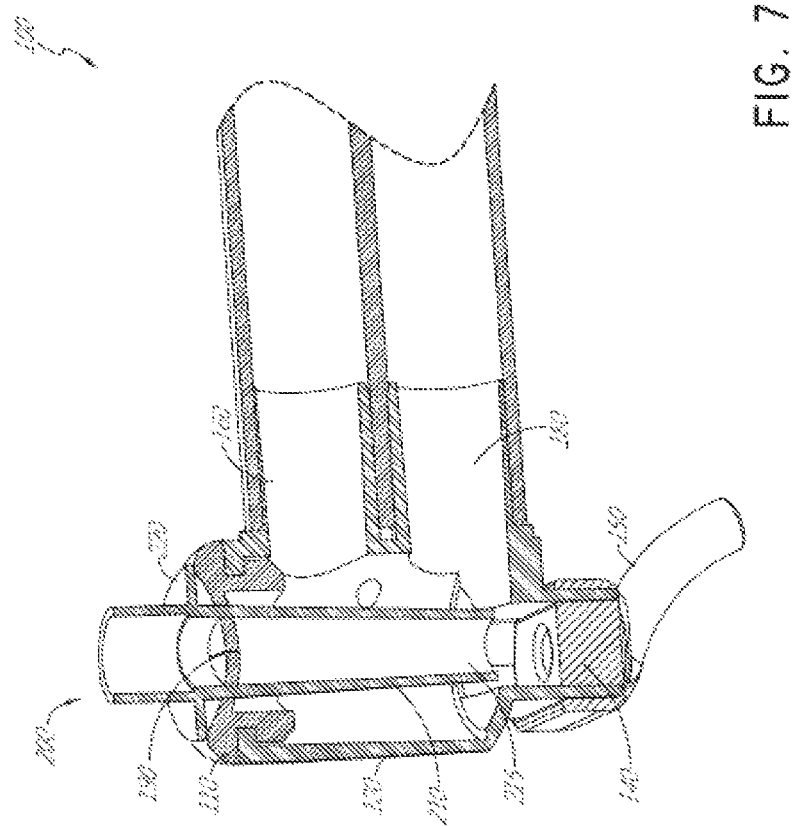
FIG. 7 illustrates a cross-section of an adaptor including a removable nozzle according to an embodiment of the disclosure.
Figure 11:
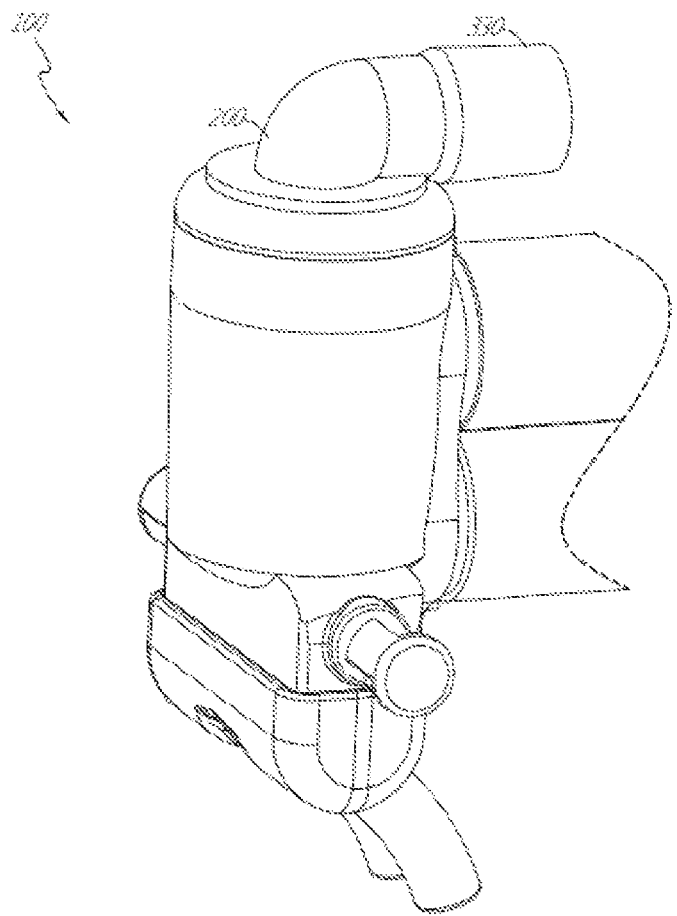
FIG. 11 illustrates a perspective view of an adaptor according to another embodiment of the disclosure.
Figure 12:
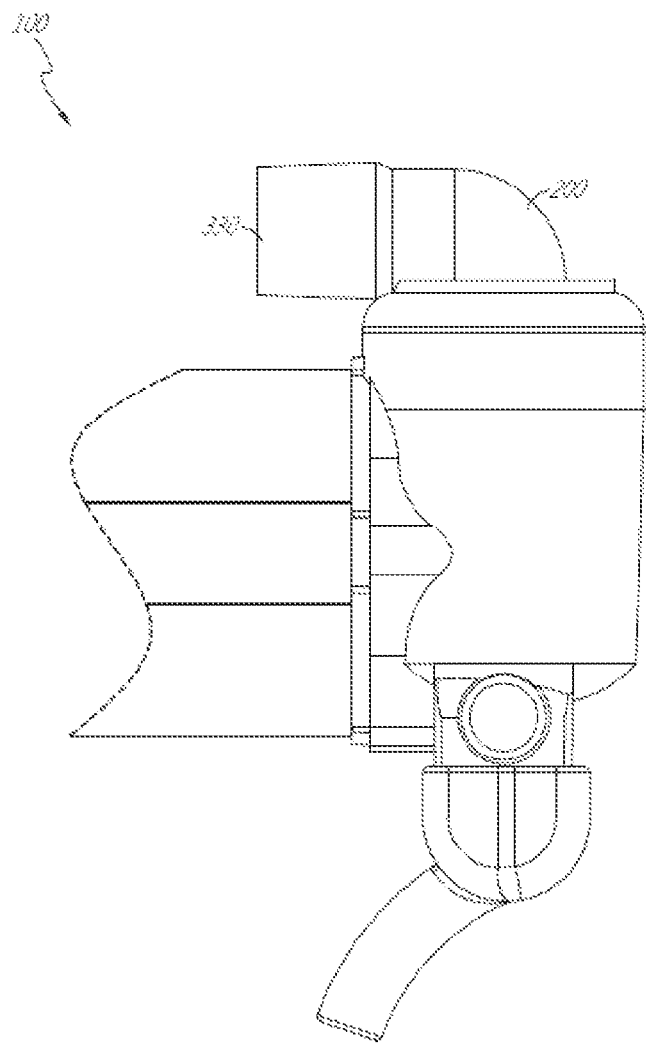
FIG. 12 illustrates a side view of the adaptor of FIG. 11.

FIG. 7 illustrates an example of the interaction between the nozzle 200 and the adaptor 100. The inclusion and/or configuration of the intermediate tube system is merely illustrative and is by no means limiting. As will be described in more detail below, the nozzle 200 can include a body 210, a second end 215, and a ledge 220. In some embodiments, the ledge 220 rests on the sealing portion 110 of the adaptor 100 when the nozzle 200 is inserted into the housing 120. The second end 215 of the body 210 can open near the first end of the coupling surface 140. In some embodiments, this arrangement can reduce aerosol deposition within the adaptor 100 and the patient interface 150 by reducing the distance and optimising the geometry through which the aerosol travels, and by reducing the mixing between the aerosol and the respiratory gases. This can also reduce the impact of incorrectly connecting the intermediate tube system, or the inspiratory tube 6 and the expiratory tube 4. By positioning the second end 215 of the body 210 near the first end of the coupling surface 140, the aerosolised gases can be directed into the patient interface 150 and are less affected by the direction of the gases flow. In some embodiments, the distance between the second end 215 of the body 210 and the first end of the coupling surface 140 can be between about 3 mm to about 10 mm. In some embodiments, the second end 215 is positioned between an entrance to the patient interface 150 and any other port, including, for example, inlet port 160 and outlet port 180. In some examples, the valve 190 can be pushed open when the nozzle 200 is inserted (not illustrated). When the nozzle 200 is removed, the valve 190 can stay closed to prevent the loss of CPAP when the nozzle 200 is connected to the device.

The illustrated nozzle 200 can be a tubular structure that is positioned within the cylindrical housing 120. In some embodiments, the nozzle 200 can have a circular cross-section which provides no sharp edges and therefore can reduce deposition within the nozzle. The nozzle 200 is not limited to a tubular shape and can include any number of different shapes. In some examples, the arrangement of the nozzle 200 within the cylindrical housing 120 can maximize gases flow about the nozzle 200. For example, inspiratory gases can enter the housing 120 via the inlet port 160 and move around the nozzle 200 towards the patient interface 150. In some embodiments, the expiratory gases can then exit the patient interface 150 and move around the nozzle 200 toward the outlet port 180, to be carried away by the expiratory tube 4.

The nozzle 200 can be configured to couple with a medicament delivery device via a tube. An example of the tube is described in International Application WO2014/088430 and International Application WO2012/164407. The entireties of both of these international patent applications are hereby incorporated by reference in their entirety. Alternatively, the tube can be any tube that can be configured to couple with the first end of the nozzle 200. In some embodiments, the nozzle 200 can be configured to couple directly to a medicament delivery device. In some examples, the inner diameter of the tube can be in the range of about 4 mm to about 12 mm. In some embodiments, the inner diameter of the tube can be in the range of about 1 mm to about 20 mm.

FIGS. 8-10 illustrate embodiments of the nozzle 200. As noted above, the nozzle 200 can include a body 210 and a ledge 220. A first end of the body 210 fluidly can couple with, for example, a medicament delivery device-such as a nebuliser, a capillary aerosol generator, or a metered dose inhaler (MDI)—or a tube. In some examples, a second end 215 of the body 210 can open into the housing 120 of the adaptor 100. In some embodiments, the body 210 can form a tubular passageway that can be configured to allow gases to flow from the medicament delivery device to the adaptor 100. The body 210 can include smooth inner surfaces to reduce deposition of the aerosol within the body 210.

In some examples, the ledge 220 can abut a perimeter of the sealing portion 110 of the adaptor 100 upon insertion of the nozzle 200. The ledge 220 can prevent the nozzle 200 from being inserted too far into the housing 120. This arrangement can improve the placement of the nozzle 200 within the housing 120, which can optimize aerosol delivery to the patient.

In some embodiments, the region of the nozzle 200 located distal to the patient can include a coupling mechanism such as a thread to facilitate connection to a tube or medicament delivery device. The coupling mechanism can be located on the outer surface of the nozzle 200. In some embodiments, the coupling mechanism can be located on the inner surface of the nozzle 200. The tube or medicament delivery device can include a complementary coupling mechanism to couple with the coupling mechanism of the nozzle 200. In some embodiments, the coupling mechanism of the nozzle 200 can include a mechanical coupling such as a clip, or adhesives, to couple the nozzle 200 to the tube or medicament delivery device.

FIG. 8 illustrates an example embodiment of the nozzle 200 including a body 210, wherein a second end 215 of the body 210 has approximately the same diameter as a first end of the body 210. This arrangement can maintain an acceptable resistance to flow through the body 210 and reduce the likelihood of aerosol deposition on the inner surface of the body 210.

FIG. 9 illustrates an example embodiment of the nozzle 200 including a body 210, wherein the body 210 may taper slightly. The taper can cause the diameter of the second end 215 of the body 210 to be less than the diameter of the first end of the body 210. In some embodiments, the first end of the body 210 can have a diameter between about 3 mm to about 10 mm, and the second end of the body 210 can have a diameter between about 1 mm to about 5 mm. In some examples, the tapering of the body 210 does not have an undesirable effect on aerosol deposition or resistance to flow. The tapering of the body 210 can improve gases flow about the nozzle 200, and allow the nozzle 200 to be inserted deeper into the adaptor 100.

FIG. 10 illustrates an example embodiment of the nozzle 200. The nozzle 200 includes an angled cut-off at the second end 215. The angled cut-off facilitates easy insertion of the nozzle 200 into the sealing portion 110. Depending on the angle of the cut-off, the size of the opening at the second end 215 can be larger when compared with the embodiments illustrated in FIGS. 8-9. In some embodiments, this can increase the volume of gases released from the second end.

Figure 16:
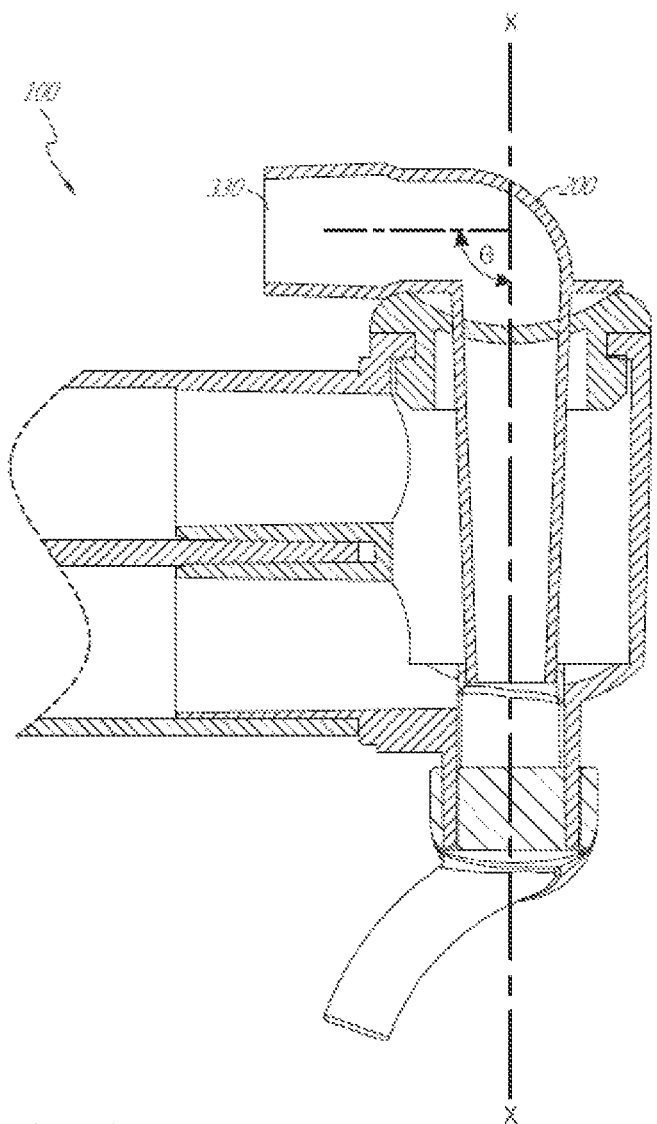
FIG. 16 illustrates a side cross-sectional view of the adaptor of FIG. 11.

FIGS. 11-16 illustrate an example of the adaptor 100 with a connector 330. In some examples, the connector 330 can be attached to the nozzle 200. In some embodiments, the connector 330 can be configured to couple a tube to the nozzle 200. The connector 330 can provide an angled connection that is configured to couple the tube to the nozzle 200, as shown more clearly in FIG. 16. An angle θ represents the orientation of the tube 330 with reference to an axis of the adaptor 100 indicated by the dotted line X-X. As illustrated in FIG. 16, the adaptor 100 can have an axis X-X. In some embodiments, the axis X-X can be considered to be substantially vertical. In some embodiments, the angle θ is approximately 90°. In some embodiments, the angle θ is between approximately 90° and 180° inclusive. The angled connector 330 can allow a connected tube to be positioned at a greater distance from the patient by directing the tube away from the patient, which can reduce the bulk at or near the patient. In some embodiments, a tube connected to the connector 330 can be attached to a patient interface stabilising mechanism, the inspiratory tube 6, or the expiratory tube 4. The aforementioned connection can keep the connector 330 from obstructing the patient or user. In some examples, a tube connected to the connector 330 can be left to naturally position itself. In some embodiments, a tube can be integrated with the connector 330.

In some embodiments, the length of the tube connected to the connector 330 can be optimised to reduce medicament deposition on the inner walls of the tube without causing patient discomfort. In some examples, a longer length of tube can allow the medicament delivery device to be positioned at a distance from the patient. For example, the longer length of tube can allow the medicament delivery device to be positioned at or near the humidification apparatus 3, which increases patient comfort by reducing the bulk and weight of the device at the patient. In some embodiments, a shorter length of tube can be configured to position the medicament delivery device proximal, or at the closer end, to the patient. For example, the medicament delivery device can be positioned at or near the adaptor 100 so as to allow direct connection of the medicament delivery device to the adaptor 100. The closer proximity of the medicament delivery device to the patient can reduce aerosol deposition in the adaptor 100 and improve delivery of the aerosol to the patient.

The medicament delivery device can be a variety of structures. For example, the medicament delivery device can be a nebuliser, capillary aerosol generator, or MDI. A nebuliser such as a flow based nebuliser, for example, can deliver aerosolised surfactant to the patient. In some embodiments, a nebuliser can be configured to deliver a medicament, or anaesthetic substance to the patient.

In some embodiments, the nozzle 200 is a part of a medicament delivery device kit, for example, a nebuliser kit. For example, when the decision is made to aerosolise the patient, a nebulising kit can be opened and the nozzle 200 can be inserted into the adaptor 100. The inclusion of the nozzle 200 in the nebulising kit can reduce waste, as the kit is only opened if the decision to nebulise the patient is made. In some embodiments, the nozzle 200 can be individually packed and used as needed. In some embodiments, the nozzle 200 is included with the adaptor 100, which provides a simple option that keeps the complementary parts together.

Use of an integrated system to deliver gases to a patient can improve usability and reduce patient discomfort. For example, the adaptor 100 can be designed to deliver sufficient gases to the patient in normal use. Thus, the adaptor 100 can remain in place during the ventilation of the patient. The nozzle 200 can be introduced to the adaptor 100 in a way that does not substantially impact the ventilation of the patient, but allows delivery of aerosolised gases, such as medicaments or aerosolised surfactant, while continuing ventilation.

In some embodiments, the nozzle 200 can be permanently integrated with the adaptor 100. The nozzle 200 can be configured to directly couple to a medicament delivery device. In some examples, the nozzle 200 can be sealed using a cap. The system can be a single piece that can optimize aerosol delivery to the patient without restricting gases flow. In some embodiments, the cap can be coupled to the adaptor 100 using a tether or a chain.

In some embodiments, the adaptor 100 with the permanently integrated nozzle 200 can be combined with a modulating piece which can facilitate connection with the medicament delivery device. The modulating piece can include an additional nozzle or tube which couples with the permanent nozzle 200 and facilitates a fluid connection between the adaptor 100 and the medicament delivery device. In some examples, the permanent nozzle 200 can be sealed with a cap or a valve. In some embodiments, a valve seals the system regardless of whether the medicament delivery device is coupled with the adaptor 100.

Although the present disclosure describes an adaptor for use with a respiratory system, embodiments of the adaptor may be used with other medical systems, for example, a surgical system such as for laparoscopic or open surgery.

Figure 18A:
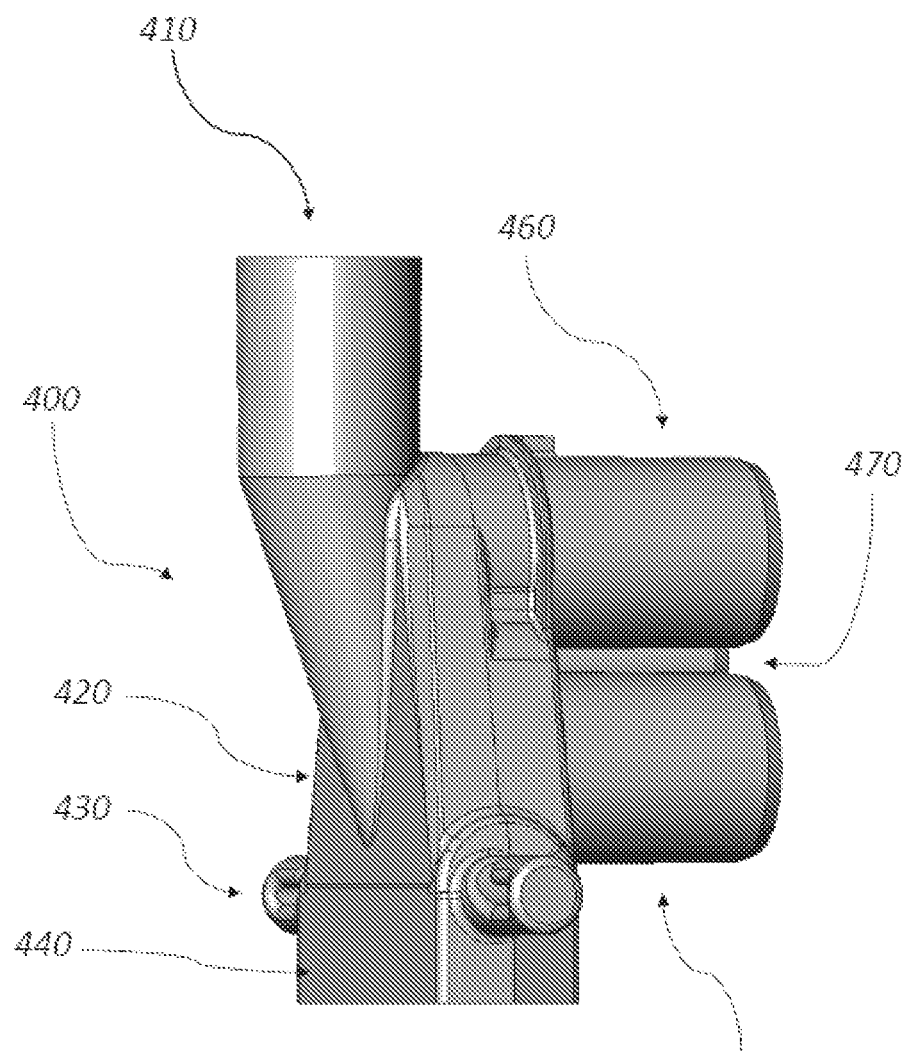
FIG. 18A illustrates a side view of an embodiment of an adaptor for a respiratory system.
Figure 18B:
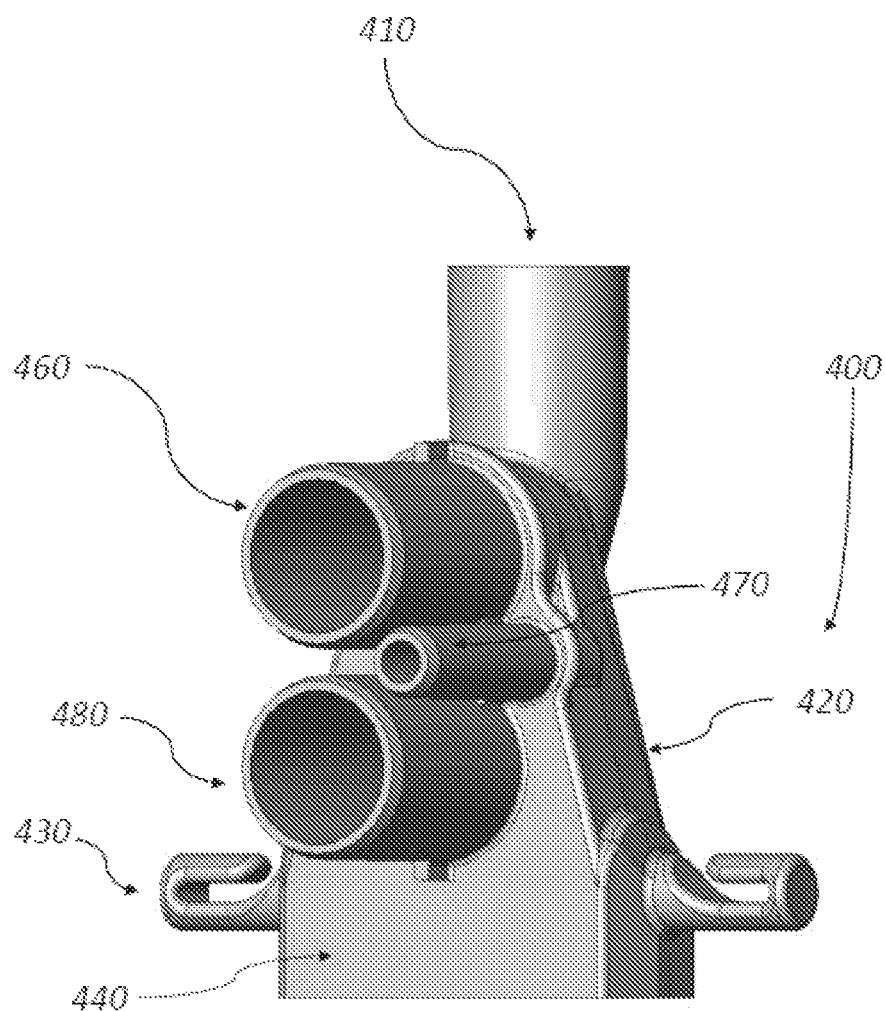
FIG. 18B illustrates a front perspective view of the adaptor for a respiratory system of FIG. 18A.

FIGS. 18A-18B illustrate another embodiment of the adaptor 400 in which the adaptor 400 includes a permanently integrated nozzle 410. The adaptor 400 is generally similar to the adaptor 100 described above and can include a body 420, a plurality of clips 430, an inlet port 460, a pressure port 470, an outlet port 480, and a coupling surface for engaging a patient interface (not pictured). In some embodiments, the inlet port 460 can be configured to receive an inspiratory tube 6 from a humidification apparatus. In some embodiments, the outlet port 480 can be configured to receive an expiratory tube 4 to a pressure regulating device 7. In some embodiments, the pressure port 470 can be configured to connect to a pressure line. In some embodiments, the location of the inlet port 460 and the outlet port 480 can be alternated such that the outlet port 480 is located above the inlet port 460.

Figure 18C:
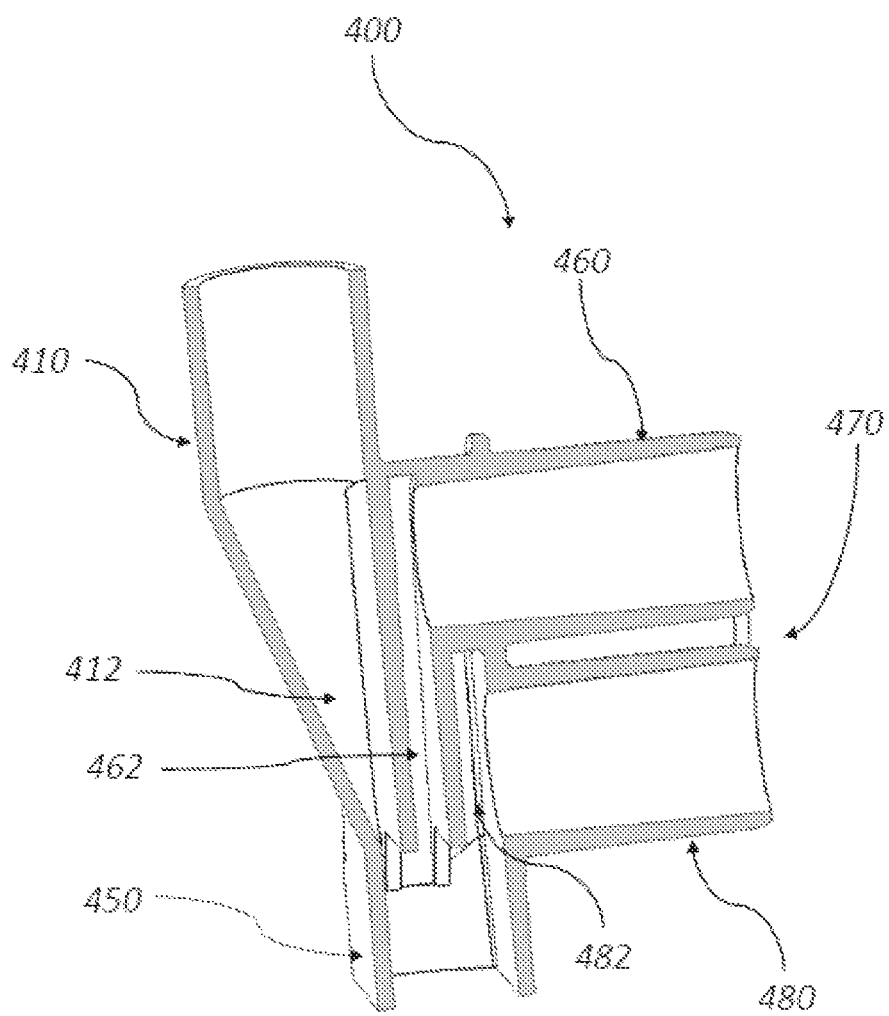
FIG. 18C illustrates a cross-sectional view of the adaptor for a respiratory system of FIGS. 18A-B.

As illustrated in FIGS. 18A and 18C, the nozzle 410 can be integrated into the body 420 such that the portion of the nozzle 410 attached to the body 420 has a decreasing radius as it nears the body 420. In some embodiments, the radius of the nozzle 410 can be decreased such that the nozzle 410 is sloped angularly towards the body 420. In some embodiments, the radius of the nozzle 410 remains largely unchanged along the length of the nozzle 410 as it is attached to the body 420. The design of the adaptor 400, as illustrated in FIG. 18C, can be configured to provide the adaptor 400 with a smaller overall profile as it does not need to accommodate the removable nozzle. In some embodiments, as illustrated in FIG. 18C, the nozzle 410 can be offset from a centerline or central region of the adaptor 400 such that a center axis of the nozzle 410 is not coaxial with the centerline or central region of the adaptor 400. This can also provide a further reduction of size of the adaptor 400.

The body 420 of the adaptor 400 can be divided into a plurality of compartments. In some embodiments, the body 420 is divided into three compartments—the nozzle compartment 412, the inlet compartment 462, and the outlet compartment 482. The plurality of compartments of the body 420 of the adaptor 400 can reduce premixing between the drug received through the nozzle 410 and the incoming gases through the inlet port 460. As well, in some embodiments, the plurality of compartments of the body 420 of the adaptor 400 can reduce dilution of the drug by the outgoing gases through the outlet port 480.

The three compartments, the nozzle compartment 412, the inlet compartment 462, and the outlet compartment 482, can be narrow so as to reduce the profile of the adaptor 400. In some embodiments, the nozzle compartment 412 is formed from the interior walls of the nozzle 410 and provides a fluid connection from the nozzle 410 to the interior of the body 420. In some embodiments, the inlet compartment 462 shares a common wall with the nozzle compartment 412 and can provide a fluid connection from the inlet port 460 to the interior of the body 420. In some embodiments, the outlet compartment 482 shares a common wall with the inlet compartment 462 and can provide a fluid connection from the outlet port 480 to the interior of the body 420.

Figure 19A:
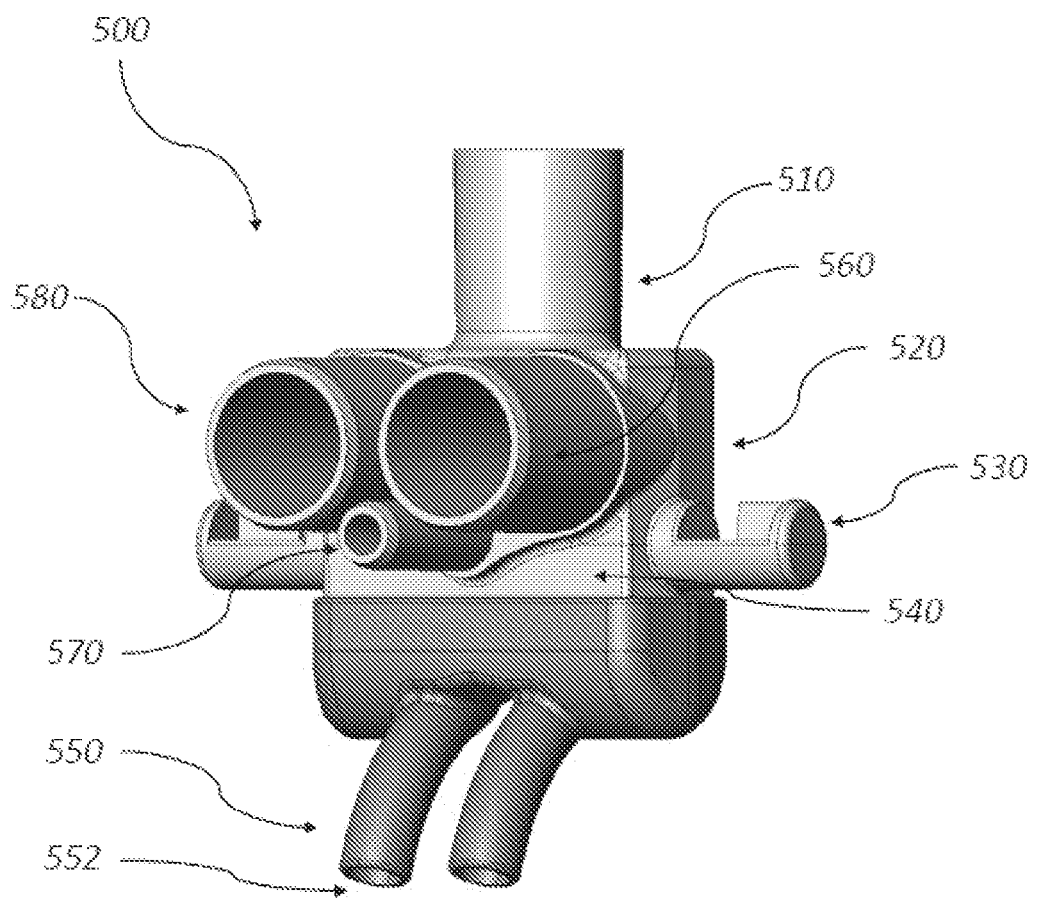
FIGS. 19A and 19B illustrates a front perspective view and a cross-sectional view of an embodiment of an adaptor for a respiratory system.
Figure 19B:
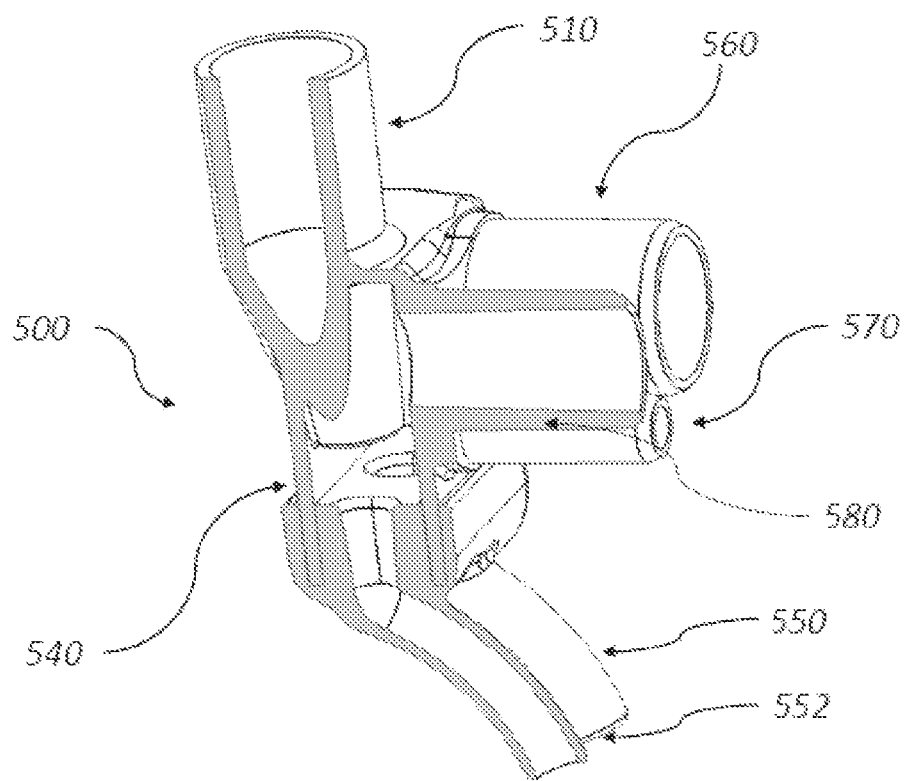
Figure 20A:
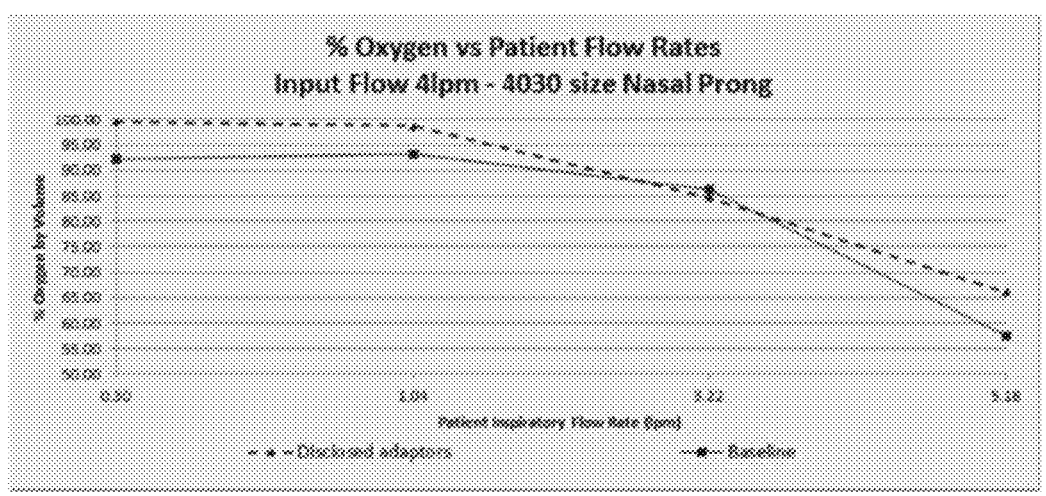
FIGS. 20A-20E graphically illustrate the amount of dilution that occurs for different embodiments of adaptors over different flow rates, wherein oxygen flow simulates drug delivery.
Figure 20B:
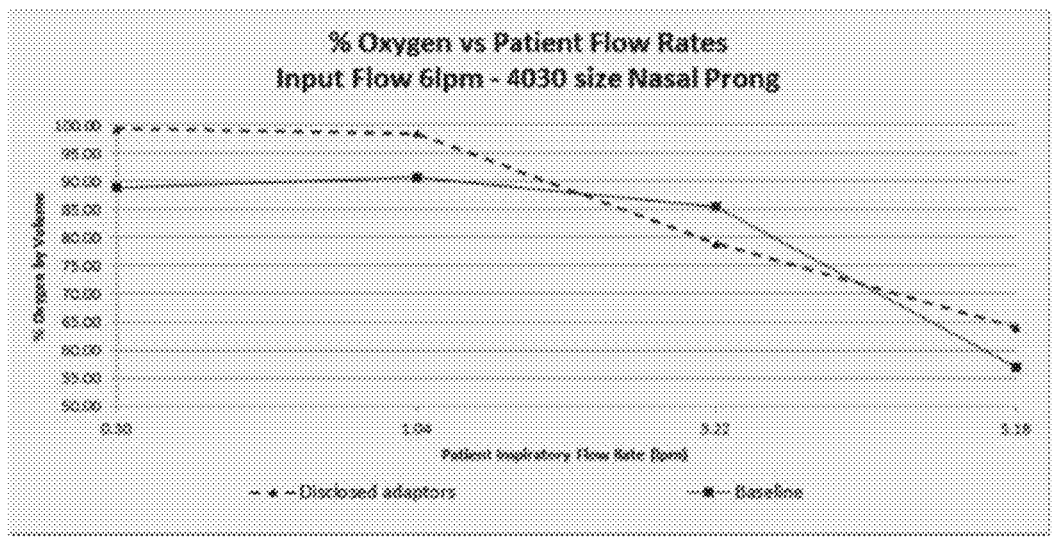
Figure 20C:
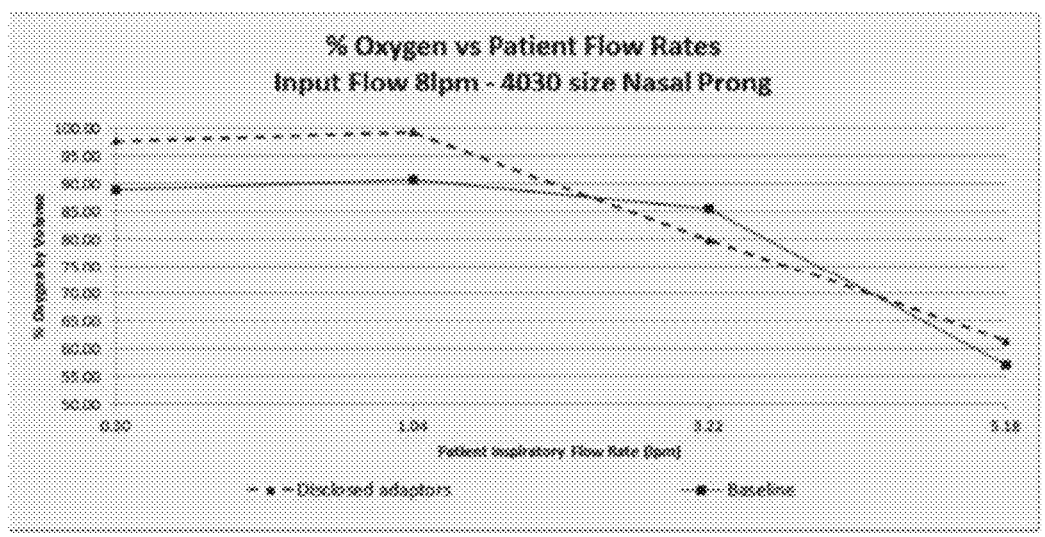
Figure 20D:
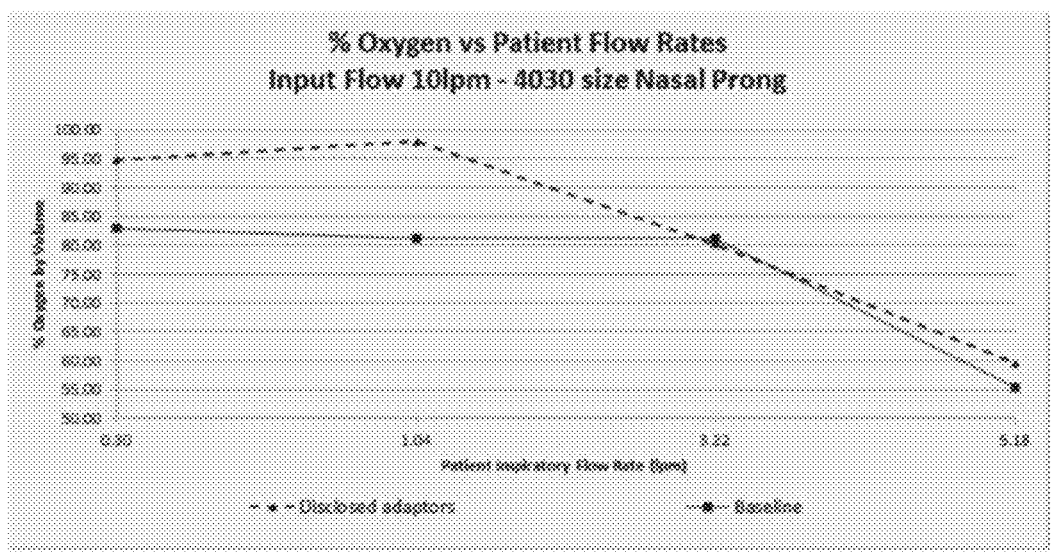
Figure 20E:
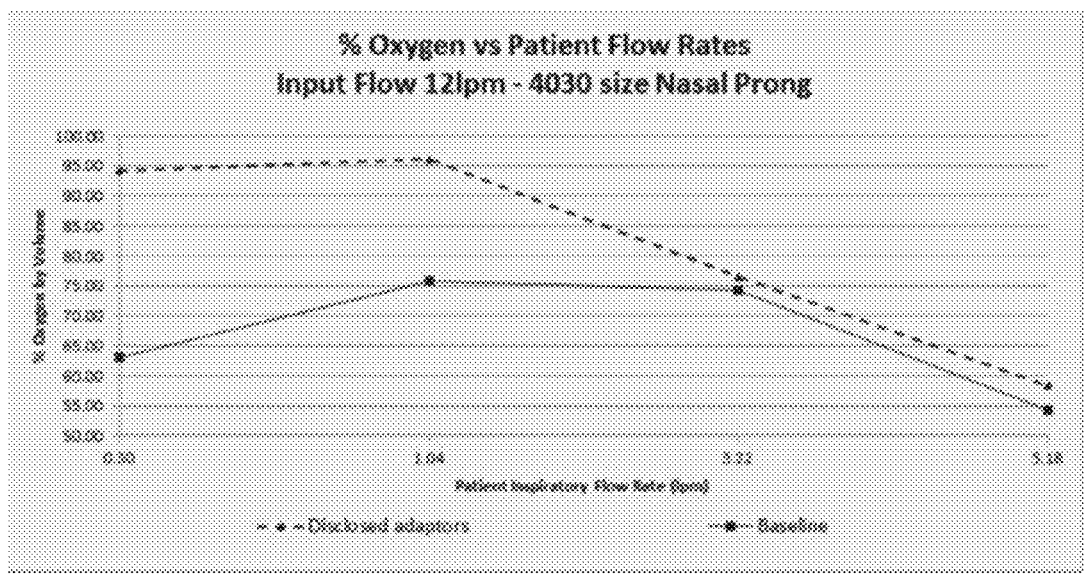

FIGS. 19A-19B illustrate another embodiment of the adaptor 500 in which the nozzle 510 is integrated into the adaptor 500. The adaptor 500 can include a body 520, a plurality of clips 530, an inlet port 560, a pressure port 570, an outlet port 580, and a coupling surface 540 for engaging with a patient interface 550. In some embodiments, the patient interface 550 includes a plurality of nostril ports 552 that are configured to provide a patient with gas flow (see FIG. 1). In some embodiments, the inlet port 560 can be configured to receive an inspiratory tube 6 from a humidification apparatus. In some embodiments, the outlet port 580 can be configured to receive an expiratory tube 4 to a pressure regulating device 7. In some embodiments, the pressure port 570 can be configured to connect to a pressure line. In some embodiments, the location of the inlet port 560 and the outlet port 580 can be alternated such that the inlet port 560 is located to the left of the outlet port 580.

The adaptor 500 of FIGS. 19A-19B is largely similar to the adaptor 100 and adaptor 400 except that the inlet port 560 and the outlet port 580 are positioned horizontally on the body 520. As shown in the cross-section of adaptor 500 in FIG. 19B, the nozzle 510 can be offset from a centerline or central region of the body 520 such that a center axis of the nozzle 510 is not coaxial with the centerline or central region of the body 520. This configuration can prevent the drugs received from the nozzle 510 from mixing with the gases from the inlet port 560 and outlet port 580. As well, as in the adaptor 400, the integration of the nozzle 510 into the body 520 can help to reduce the volume within the adaptor 500 and can thus improve the clearance of dead space. Although the adaptor 500 can appear bulkier at the patient's face because of the increased width, the reduction of dead space within the adaptor 500 can reduce the build-up of carbon dioxide within the body 520.

As will be discussed in more detail below, the position of the nozzle exit relative to the nostril ports of the patient interface can affect the dilution of the drug. For example, drugs are less likely to be diluted where the nozzle exit is closer to the nostril ports of the patient interface than where the nozzle exit is further away from the nostril ports of the patient interface. The structure of the presently disclosed embodiments includes an adaptor with a reduced distance between the exit point of the nozzle and the entry point of the patient interface (for example, the nasal prongs) as compared to other devices currently on the market. For example, for one or more of the disclosed embodiments, the distance between the exit point of the nozzle and entry point of the patient interface can be less than about 10 mm, less than about 5 mm, or less than about 3 mm. This reduced distance between the nozzle and patient interface has been shown to reduce the amount of dilution of the delivered drug as it provides less opportunity for air from the inspiratory tube to intermix with the delivered drug.

As well, in some embodiments, the position of the inspiratory tube and expiratory tube can affect the amount of dilution that occurs. As illustrated in FIGS. 6-7 and 18A-C, the adaptors 100, 400 include inlet ports 160, 460 and the outlet ports 180, 480 that are configured to provide gases flow through the body of the adaptors 100, 400 in the same direction as the flow of the drug being delivered through the nozzle 200, 410. This positioning of the inlet ports 160, 460 and the outlet ports 180, 480 can prevent additional dilution of the drug being delivered through the nozzle 200, 410 as the air flowing through the inspiratory tube is not encouraged to intermix with the drug flow.

FIGS. 20A-20E illustrate the reduction in drug dilution in our disclosed adaptors. Unlike existing adaptors on the market, the presently disclosed adaptors have a decreased distance between the nozzle and patient interface as well as inlet and outlet ports that cause the inspiratory gases to flow in the same direction as the drug through the nozzle.

FIGS. 20A-20E compare the percentage of drug a patient inspires using the adaptors disclosed in the present application when compared to existing adaptors on the market. The comparison is done over different inspiratory tube flow rates and across a range of patient inspiratory flow rates. In each graph, oxygen flow is used to simulate drug delivery. The graphs illustrate the performance of adaptors 100, 400 ("disclosed adaptors") when compared to existing adaptors on the market ("baseline").

FIG. 20A illustrates a graph of the dilution of delivered drug (simulated by the percent of oxygen by volume) over a range of "Patient Inspiratory Flow Rates" as measured in liters per minute (lpm). The graph of FIG. 20A illustrates the test conducted with an input flow rate through the inspiratory tube of 4 lpm using a 4030 size Nasal Prong.

FIG. 20B illustrates a graph of the dilution of delivered drug (simulated by the percent of oxygen by volume) over a range of "Patient Inspiratory Flow Rates" as measured in liters per minute (lpm). The graph of FIG. 20B illustrates the test conducted with an input flow rate through the inspiratory tube of 6 lpm using a 4030 size Nasal Prong.

FIG. 20C illustrates a graph of the dilution of delivered drug (simulated by the percent of oxygen by volume) over a range of "Patient Inspiratory Flow Rates" as measured in liters per minute (lpm). The graph of FIG. 20C illustrates the test conducted with an input flow rate through the inspiratory tube of 8 lpm using a 4030 size Nasal Prong.

FIG. 20D illustrates a graph of the dilution of delivered drug (simulated by the percent of oxygen by volume) over a range of "Patient Inspiratory Flow Rates" as measured in liters per minute (lpm). The graph of FIG. 20D illustrates the test conducted with an input flow rate through the inspiratory tube of 10 lpm using a 4030 size Nasal Prong.

FIG. 20E illustrates a graph of the dilution of delivered drug (simulated by the percent of oxygen by volume) over a range of "Patient Inspiratory Flow Rates" as measured in liters per minute (lpm). The graph of FIG. 20E illustrates the test conducted with an input flow rate through the inspiratory tube of 12 lpm using a 4030 size Nasal Prong.

In each of the aforementioned graphs, the flow rate of the drug delivered through the nozzle is 3 lpm. The flow rate of drug delivery is limited by third party products on the market. Therefore, at patient inspiratory flow rates below the flow rate of the drug delivered (in this instance, below 3 lpm), no drug dilution should be observed if the adaptor is efficiently delivering the drug directly from the nozzle to the patient. At patient inspiratory flow rates above the flow rate of the drug delivered (in this instance, above 3 lpm), drug dilution will naturally be observed as part of the air being inspired by the patient will partially include air from the inspiratory tube.

As drug dilution is expected at higher patient inspiratory flow rates (in this instance, above 3 lpm), the efficiency of the structure of the adaptor and its ability to prevent drug dilution is best observed at low patient inspiratory flow rates. As seen in FIGS. 20A-20E, across all input flow rates through the inspiratory tube, significantly more drug dilution is observed in existing adaptors on the market. Particularly as the input flow rate through the inspiratory tube is increased from 4 lpm through 12 lpm, the performance of existing adaptors on the market drops precipitously from approximately 93% drug delivery at an input flow rate of 4 lpm to a dismal drug delivery of approximately 64% at an input flow rate of 12 lpm.

In comparison, the disclosed adaptors 100, 400 consistently deliver over 90%-95% of the drug to the patient at inspiratory low flow rates. As discussed above, the disclosed adaptors decrease the distance between the nozzle and the patient interface and provides an input flow through the inspiratory tube that is in the same direction as the drug delivery. These structural aspects help to prevent intermixing of the gases through the inspiratory tube with the drug delivered through the nozzle.

It should be noted that various changes and modifications to the presently preferred embodiments described herein will be apparent to those skilled in the art. Such changes and modifications may be made without departing from the spirit and scope of the apparatus and systems of the disclosure and without diminishing its attendant advantages. For instance, various components may be repositioned as desired. It is therefore intended that such changes and modifications be included within the scope of the apparatus and systems of the disclosure. Moreover, not all of the features, aspects and advantages are necessarily required to practice the present apparatus and systems of the disclosure. Accordingly, the scope of the present apparatus and systems of the disclosure is intended to be defined only by the claims that follow.

Reference to any prior art in this specification is not, and should not be taken as, an acknowledgement or any form of suggestion that that prior art forms part of the common general knowledge in the field of endeavour in any country in the world.

Wherein the foregoing description reference has been made to integers or components having known equivalents thereof, those integers are herein incorporated as if individually set forth.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The apparatus and system of the disclosure may also be said broadly to consist in the parts, elements and features referred to or indicated in the specification of the application, individually or collectively, in any or all combinations of two or more of said parts, elements or features.

What is claimed is:

1. A respiratory system comprising:
   an inspiratory tube;
   an expiratory tube;
   a patient interface configured for delivery of respiratory gases and aerosolized substances to a patient;
   an adaptor joining the inspiratory tube, the expiratory tube, and the patient interface; and
   a nozzle comprising:
      a body comprising a first end and a second end, wherein the first end is configured to couple with a medicament delivery device, wherein the second end is fluidly connected to the patient interface and a pressure port adjacent to the patient interface; and
      a ledge that is configured to rest on a sealing portion of the adaptor,
   wherein the nozzle is configured to be inserted into the adaptor such that the second end of the body of the nozzle is closer to the expiratory tube and the patient interface than to the inspiratory tube.

2. The respiratory system of claim 1, wherein the nozzle is connected to the medicament delivery device and the medicament delivery device is at least one of a nebulizer, a capillary aerosol generator, and a metered dose inhaler.

3. The respiratory system of claim 1, wherein the second end forms an angled cut-off.

4. The respiratory system of claim 1, wherein the body of the nozzle includes a smooth inner surface.

5. The respiratory system of claim 1, wherein the nozzle has a cylindrical structure or a frustoconical structure.

6. The respiratory system of claim 1, wherein the body is tapered.

7. The respiratory system of claim 1, wherein the nozzle has a length defined between the second end of the body and the ledge such that the nozzle is configured to open near the first end of a coupling surface of the adaptor and the coupling surface is configured to be coupled to the patient interface.

8. The respiratory system of claim 7, wherein a distance between the second end of the body and the first end of a coupling surface of the adaptor is between about 3 mm to about 10 mm.

9. The respiratory system of claim 7, wherein the second end is sized and shaped to be positioned between an entrance to the patient interface and any other port of the adaptor.

10. The respiratory system of claim 7 in combination with the patient interface and the adaptor, wherein the patient interface comprises nasal prongs which can be integrated permanently with the adaptor.

11. The respiratory system of claim 1 in combination with the adaptor, wherein the second end of the body can open into a housing of the adaptor.

12. The respiratory system of claim 11, wherein the ledge abuts a perimeter of the sealing portion of the adaptor upon insertion of the nozzle into the adaptor.

13. The respiratory system of claim 1 in combination with the medicament delivery device, the nozzle further comprising a coupling feature, wherein the coupling feature can couple the nozzle with the medicament delivery device.

14. The respiratory system of claim 1, wherein the nozzle is insertable through a valve of the sealing portion.

15. The respiratory system of claim 14, wherein an outer surface of the nozzle is sealed by the sealing portion when the nozzle is inserted through the valve.

16. The respiratory system of claim 1, wherein the first end of the body is positioned adjacent a sealing portion of the adaptor and the second end of the body is positioned adjacent the pressure port of the adaptor, and wherein the sealing portion of the adaptor is on an opposite portion of the adaptor as the pressure port.

17. The respiratory system of claim 1, wherein an inlet port and an outlet port are positioned between the first end of the body and the pressure port.

18. A respiratory system for delivering medicament from a medicament delivery device to a patient, the system comprising:
   an inspiratory tube;
   an expiratory tube;
   a pair of nasal prongs configured for delivery of respiratory gases and aerosolized substances to a patient;
   an adaptor joining the inspiratory tube, the expiratory tube, and the pair of nasal prongs;
   a nozzle comprising:
      a body comprising a first end and a second end, wherein the first end is configured to receive medicament and the second end is fluidly connected to the pair of nasal prongs and a pressure port adjacent to the pair of nasal prongs; and
      a ledge that is configured to rest on a sealing portion of the adaptor, wherein the ledge forms a perimeter about the body, and wherein the nozzle is configured to be inserted into the adaptor such that the second end of the body of the nozzle is closer to the expiratory tube and the pair of nasal prongs than to the inspiratory tube.

* * * * *